US008802939B2

(12) United States Patent
Phan et al.

(10) Patent No.: US 8,802,939 B2
(45) Date of Patent: Aug. 12, 2014

(54) HYBRID PEPPER PLANTS RESULTING FROM A CROSS BETWEEN C. ANNUUM AND C. PUBESCENS

(75) Inventors: Chuong Phan, Davis, CA (US); John Kao, Davis, CA (US); Terry Berke, Zamora, CA (US); Carl Jones, Davis, CA (US)

(73) Assignee: Seminis Vegetable Seeds, Inc., St. Louis, MI (US)

( * ) Notice: Subject to any disclaimer, the term of this patent is extended or adjusted under 35 U.S.C. 154(b) by 262 days.

(21) Appl. No.: 12/549,156

(22) Filed: Aug. 27, 2009

(65) Prior Publication Data
US 2010/0058494 A1    Mar. 4, 2010

Related U.S. Application Data

(60) Provisional application No. 61/093,122, filed on Aug. 29, 2008.

(51) Int. Cl.
*A01H 1/04* (2006.01)
*A01H 4/00* (2006.01)
*A01H 5/00* (2006.01)
*A01H 5/10* (2006.01)

(52) U.S. Cl.
USPC ........ 800/317.1; 800/265; 800/268; 800/269; 435/410

(58) Field of Classification Search
None
See application file for complete search history.

(56) References Cited

U.S. PATENT DOCUMENTS 5,066,830 A    11/1991   Morrison et al.

FOREIGN PATENT DOCUMENTS

WO    WO 2007/038980 A1    4/2007

OTHER PUBLICATIONS

Rawson et al, eds. Sterility in Wheat in Subtropical Asia: Proceedings of a workshop Sep. 18-21, 1995, Pokhara, Nepal; pp. 13-31.*
Molchova. E. (1967) Bulgarian Academy of Sciences Press, pp. 91-98, Abstract relied upon.*
Belleti et al, eds. Capsicum Newsletter No. 1, p. 21 (1982).*
Mimura et al. Breeding Science 62: 93-98 (2012).*
PI 586661 (1995).*
PI 592817 (1996).*
PI 635840 (2004).*
PI 635844 (2004).*
Biosis Search Results (May 2013).*
Andrasfalvy et al., "Cytoplasmic systems of interspecific hybrids in Capsicum, reconsidered," *Eucarpia Vth Meeting on Genetics and Breeding of Capsicum and Eggplant*, Plovdiv, Bulgaria, pp. 18-20 (1983).
Bermawie et al., "Post-fertilization breakdown in interspecific crosses between *C. chacoense* and two purple-flowered species (*C pubescens* and *C. tovarii*)", *Plant Breeding Abstracts* vol. 061, Abs. No. 01867 (1989).
Bodhipadma et al., "In Vitro Fruiting and Seed Set of *Capsicum Annuum* L. CV. Sweet Banana," *In Vitro Cell. Dev. Biol.—Plant*, 39:536-539 (2003).
Cheung et al., "Genetic Analysis and Breeding for Resistance to Bacterial Wilt in *Capsicum* Pepper," *HortScience* 34(3):445 Abstract 026 (1999).
Cho et al., "Resistance to Gray Leaf Spot in *Capsicum* Peppers," *HortScience* 36(4):752-754 (2001).
Csillery, "A contribution to the list of the possible interspecific crosses in *Capsicum*," *Eucarpia Vth Meeting on Genetics and Breeding of Capsicum and Eggplant*, Plovdiv, Bulgary, pp. 15-17 (1983).
Csillery et al., "On the Possibilities of *Capsicum* Breeding," *Genetica Agraria* 40(4):445 (1986).
Eshbaugh, "XII. Genetic and Biochemical Systematic Studies of Chili Peppers (*Capsicum*-Solanaceae)," *Bull. Torrey Bot. Club*, 102(6):396-403 (1976).
Garcés-Claver et al., "Determination of Capsaicin and Dihydrocapsaicin in *Capsicum* Fruits by Liquid Chromatography—Electrospray/Time-of-Flight Mass Spectrometry," *J. Agric. Food Chem.* 54:9303-9311 (2006).
"Genetic Resources of *Capsicum*," *International Board for Plant Genetic Resources* 1-49 (1983).
Heiser et al., "The Cultivated *Capsicum* Peppers," *Economic Botany*, 7(3):214-227 (1953).
Kim et al., "Development of SCAR Markers for Early Identification of Cytoplasmic Male Sterility Genotype in Chili Pepper (*Capsicum annuum* L.)," *Mol. Cells*, 20(3):416-422 (2005).
Kim et al., "Isolation and characterization of the cytoplasmic male sterility-associated orf456 gene of chili pepper (Capsicum annuum L.)," *Plant Mol. Biol.*, 63(4):519-532 (2007).
Molkhova et al., Otdalechena khibridizatsiia pri rasteniiata: materiali of Simpozium po otdalechena khibridizatsiia s mezhdunarodno uchastie, 317-336 (Yotgovooren redaktor Iordanka Georgieva-Todorove ed., Izd-vo na Bulgarskata akademiia na naukite (1983)), (translation from Bulgarian) (1983).
Muhyi et al., "Evaluation of *Capsicum* Germplasm for Sources of Resistance to *Rhizoctonia solani*," *HortScience* 30(2):341-342 (1995).
Mur et al., "The hypersensitive response; the centenary is upon us but how much do we know?," *Journal of Experimental Botany* 59(3):501-520 (2008).
Onus et al., "Unilaterial Incompatibility in *Capsicum* (Solanaceae): Occurrence and Taxonomic Distribution," *Annals of Botany*, 94(2):289-295 (2004).
Pickersgill, "Genetic resources and breeding of *Capsicum* spp.," *Emphytica* 96:129-133 (1997).

(Continued)

*Primary Examiner* — David T Fox
(74) *Attorney, Agent, or Firm* — Matthew L. Madsen; Arnold & Porter LLP

(57) ABSTRACT

The present invention relates to novel methods of producing interspecific hybrids between *C. annuum* and *C. pubescens* and progeny thereof. In addition, the present invention provides for the hybrid pepper plants, and parts thereof including their fruit, tissues, and seeds, resulting from a cross between *C. annuum* and *C. pubescens* that have nuclear genetic material from both *C. annuum* and *C. pubescens*. The hybrid pepper plants of the invention may have a variety of traits including resistance to geminiviruses, tobamoviruses, and resistance to damage by *Xanthomonas*.

36 Claims, 6 Drawing Sheets

(56) References Cited

OTHER PUBLICATIONS

Sahin et al., "Resistance in *Capsicum pubescens* to *Xanthomonas campestris* pv. *vesicatoria* Pepper Race 6," *Plant Disease* 82(7):794-799 (1998).

Sung et al., "Capsaicin biosynthesis in water-stressed hot pepper fruits," *Bot. Bull. Acad. Sin.*, 46:35-42 (2005).

Walsh et al., "Phylogenetic Relationships of *Capsicum* (Solanaceae) Using DNA Sequences from Two Noncoding Regions: The Chloroplast *atpB-rbcL* Spacer Region and Nuclear *waxy* Introns," *Int. J. Plant Sci.*, 162(6):1409-1418 (2001).

Yoon et al., "Interspecific Cross Compatibility Among Five Domesticated Species of *Capsicum* Genus," *J. Kor. Soc. Hort. Sci.*, 45(6):324-329 (2004).

Yoon et al., "Backcross introgression lines between *Capsicum annuum* and *C. baccatum* for breeding chili pepper resistant to anthracnose (*Colletotrichum* spp.)," Sep. 18, 2007.

DeVerna et al., "Sexual hybridization of *Lycopersicon-esculentium* and *Solanum-rickii* by means of a sesquidiploid bridging hybrid," *Proceedings of the National Academy of Science of the United States of America* 87(23):9486-9490 (1990).

Dinu et al., "Novel inter-series hybrids in *Solanum*, section *Petota*," *Theor. Appl. Genet.* 110(3):403-415 (2005).

International Search Report issued in Application No. PCT/US2009-055249 on Mar. 3, 2010.

Molchova et al., "On the interspecific crossability between *Capsicum annuum* L. and *Capsicum pubescens* R. & P.; *Capsicum annuum* L. and *Capsicum pendulum* Willd," *Capsicum Newsletter*, 1:1-99 at 38-41 (1982) retrieved from the Internet: http://aces.nmsu.edu.chilepepperinstitute/documents/capeggnews1.pdf.

Sharma et al., "Compatibility in *Capsicum* Species," *Indian Journal of Agricultural Sciences*, 77(12):873-875 (2007).

Tong et al., "Observations on interspecific compatibility and meiotic chromosome behavior of *Capsicum buforum* and *C. lanceloatum*," *Genetic Resources and Crop Evolution*, 50(2):193-199 (2003).

Yamgar et al., "Effects of NAA and Planofix on Flowering, Flower and Fruit Drop and Fruit Set in Chilli," *J. Maharashtra agric. Univ.* 12(1):34-38 (1987).

Yoon et al., "Trispecies Bridge Crosses, (*Capsicum annuum* x *C. chinense*) x *C. baccatum*, as an Alternative for Introgression of Anthracnose Resistance from *C .baccatum* into *C. annum*," *J. Kor. Soc. Hort. Sci.* 46(1):5-9 (2005).

Yoon et al., "Overcoming Two Post-fertilization Genetic Barriers in Interspecific Hybridization between *Capsicum annuum* and *C. baccatum* for Introgression of Anthracnose Resistance," *Breeding Science* 56(1):31-38 (2006).

Zijlstra et al., "Pollen Tube Growth in Interspecific Crosses Between *Capsicum* Species," *Hortscience* 26(5):585-586 (1991).

Lee et al., "Construction of an Integrated Pepper Map Using RFLP, SSR, CAPS, AFLP, WRKY, rRAMP, and BAC End Sequences," *Mol. Cells*, 27:21-37 (2009).

Molkhova, "Cytoembryological Study of the Sesquidiploid Hybrid *Capsicum annuum* L. X *Capsicum pubescens* R. ET P. (3x)," Genetical Research, A Collection of Papers, Bulgarian Academy of Sciences Press (1967), (English Translation attached).

Saunders et al., "The Use of AFLP Techniques for DNA Fingerprinting in Plants," Beckman Coulter, pp. 1-9 (2001).

D.K. Maheshwari, et al., "Nematicidal activity of some phenolics on root knot, growth and yield of *Capsicum frutescens* cv. California Wonder," *Journal of Phytopathology* (1990) 129: 159-164.

J.E. Pallas, "Diurnal Changes in Transpiration and Daily Photosynthetic Rate of Several Crop Plants," *Crop Science Society of America* (1973) 13: 82-84.

Barrie T. Steer, "Diurnal Variations in Photosynthetic Products and Nitrogen Metabolism in Expanding Leaves," *Plant Physiology* (1973) 51: 744-748.

Baral et al., "Genetic Diversity of a *Capsicum* Germplasm Collection from Nepal as Determined by Randomly Amplified Polymorphic DNA Markers", *J. Amer. Soc. Hort. Sci.*, 127(3):316-324 (2002).

Belletti et al., *Capsicum & Eggplant Newsletter*, University of Turin, 13, pp. 1-147 (1994).

Eshbaugh, W. Hardy, "A Nomenclatural Note on the Genus *Capsicum*", *Taxon*, 17(1):51-52 (1968).

Jarret et al., "Revisiting the Waxy Locus and the *Capsicum Annuum* L. Complex", *Georgia Journal of Science*, 62(3):118-132 (2004).

Jarret, Robert L., "DNA Barcoding in a Crop Genebank: The *Capsicum annuum* Species Complex", *The Open Biology Journal*, 1:35-42 (2008).

Kochieva et al., "Assessment of Genetic Relationships in the Genus *Capsicum* Using Different DNA Marker Systems", Meeting on Genetics and Breeding on *Capsicum* and Eggplant, pp. 44-50 (2004).

Lippert et al., "Cytogenetics of the Vegetable Crops. Garden Pepper, *Capsicum Sp.*", *Botanical Review*, 32(1):24-55 (1966).

Livingstone et al., "Genome Mapping in *Capsicum* and the Evolution of Genome Structure in the Solanaceae", *Genetics*, 152:1183-1202 (1999).

Prince et al., "A Survey of DNA Polymorphism within the Genus *Capsicum* and the Fingerprinting of Pepper Cultivars ", *Genome*, 38(2):224-231 (1995).

Shifriss, Chen, "Male Sterility in *Capsicum*", *Capsicum and Eggplant Newsletter*, 14:11-25 (Invited Paper, 1995).

Smith et al., "Breeding Behavior of Cultivated Peppers", *American Society for Horticultural Science*, 70:286-290 (1957).

M.Sc. Thesis Abstract: Dr. Y. S. Parmar University of Horticulture & Forestry—Sloan, pp. 1-102 (1985).

Ph.D. Thesis Abstract: Dr. Y. S. Parmar University of Horticulture & Forestry—Sloan, pp. 1-65 (1985).

Coffey, Biology and Control of Powdery Mildew of Peppers, Mar. 26, 2008, 1-23.

\* cited by examiner

HYBRID PEPPER PLANTS RESULTING FROM A CROSS BETWEEN *C. ANNUUM* AND *C. PUBESCENS*

Cross-Reference to Related Applications

This application claims the benefit of and priority to U.S. application Ser. No. 61/093,122 filed Aug. 29, 2008.

FIELD OF THE INVENTION

The present invention relates to and includes novel plants and methods of their production. In particular the invention relates to the methods of producing interspecific hybrids between *C. annuum* and *C. pubescens*. The present invention also includes methods for producing crosses beyond the F1 interspecific hybrid generation having traits including resistance to geminiviruses, tobamoviruses, and damage by *Xanthomonas*. In addition, the present invention provides for and includes a hybrid pepper plant, and parts thereof including fruit, tissues, and seeds, resulting from a cross between *C. annuum* and *C. pubescens* that have nuclear genetic material from both *C. annuum* and *C. pubescens*.

BACKGROUND OF THE INVENTION

Peppers are members of the Solanacea family and the genus *Capsicum*, which includes the species *C. annuum, C. baccatum, C. cardenasii, C. chacoense, C. chinense, C. ciliatum, C. eximium, C. flexuosum, C. frutescens, C. galapagoense, C. praetermissum, C. pubescens,* and *C. tovarii*. Peppers are cultivated and used around the world as sweet peppers, such as bell peppers; or as pungent chili peppers, jalapeño peppers, and TABASCO® peppers; or as a source of dried powders of various colors, such as paprika. Cultivated peppers can be distinguished by pungency, fruit shape, color and size (see for example U.S. Pat. No. 6,498,287).

While pepper plants and their fruits, commonly referred to as "peppers", are widely grown, especially *C. annuum*, the plants are prone to a variety of diseases and are susceptible to any one or more of geminivirus infection, tobamovirus infection, and attack by *Xanthomonas*. The ability to introduce into *C. annuum* from other *Capsicum* species desirable traits, such as resistance, tolerance and immunity to disease causing agents including geminiviruses, tobamoviruses, and *Xanthomonas*, along with other desirable traits already present in *C. annuum*, is therefore advantageous. Yet the ability to crossbreed many species of pepper, and particularly the ability to cross *C. annuum* and *C. pubescens*, and obtain viable and fertile plants capable of further breeding is recognized as being limited. See Walsh B. M. and Hoot S. B., *Phylogenetic Relationships of Capsicum (Solanaceae) using DNA Sequences from Two Noncoding Regions: the Chloroplast atpB-rbcl Spacer Region and Nuclear waxy Introns*, Int. J. Plant Sci. 162(6) 1409-1418 (2001) at FIG. 2.

Until the methods described herein, the barrier to crossbreeding the genetically distant pepper species *C. annuum* and *C. pubescens* has effectively prevented preparing hybrid progeny for the purpose of introgressing desirable traits from *C. pubescens* into *C. annuum*. Some investigators even indicate that the progeny of *C. annuum×C. pubescens* crosses are completely sterile, thereby preventing the development of progeny from such plants. See e.g., Walsh B. M. and Hoot S. B. supra.

SUMMARY OF THE INVENTION

The present invention provides and includes methods to prepare hybrids between plants of *C. annuum* and *C. pubescens*. The invention includes the plants produced by such methods, and parts of such plants including the pepper fruit and its seeds. In addition, the invention includes and provides for seeds that when grown give rise to a plant produced by the methods of the invention.

Included in the present invention is a method of producing an interspecific F1 hybrid pepper plant comprising the steps of:

(a) pollinating a male sterile flower of a *C. annuum* parent selected from a *C. annuum* plant or a *C. annuum* hybrid with pollen from a *C. pubescens* plant or *C. pubescens* hybrid to form a pollinated flower;

(b) following (a), treating the pollinated flower with an auxin compound;

(c) growing the *C. annuum* parent until the pollinated flower develops into a fruit bearing a seed;

(d) harvesting the fruit bearing a seed that develops from the pollinated flower; and (e) rescuing embryonic tissue from the seed of the fruit to produce an interspecific F1 hybrid pepper plant.

Also included in the present invention is a method of producing an interspecific F1 hybrid pepper plant comprising the steps of:

(a) culturing a flower bud of a *C. annuum* parent selected from a *C. annuum* plant or *C. annuum* hybrid to obtain a *C. annuum* flower;

(b) pollinating the *C. annuum* flower of (a) with pollen from a *C. pubescens* plant or a *C. pubescens* hybrid to form a pollinated flower;

(c) following the pollination in (b), removing and subculturing the ovaries from the pollinated flower in the presence of an auxin compound and a cytokinin compound;

(d) maintaining the subcultured ovaries until fruit bearing a seed develops; and (e) rescuing immature embryo tissue from the seed of the fruit to produce an interspecific F1 hybrid pepper plant.

The methods of preparing an interspecific F1 hybrid pepper plant may further comprise: (f) crossing or selfing the interspecific F1 hybrid pepper plant, which results in the production of progeny of the direct cross between a *C. annuum* parent and a *C. pubescens* plant or hybrid.

The methods of the invention also provide for the production of plants of a first cross, second cross, and third cross. Those plants may be produced by a method comprising:

(f) preparing one or more plants of a first cross by crossing or selfing an interspecific F1 hybrid pepper plant one to three times with a *C. annuum* plant, a *C. annuum* hybrid, or a filial progeny of the interspecific F1 hybrid pepper plant (e.g., F2, F3 progeny) that has been independently selected for each crossing or selfing;

(g) selecting one or more plants of a first cross with pollen that is more fertile than that of the interspecific F1 hybrid, to produce one or more selected plants of a first cross;

(h) crossing the one or more selected plants of a first cross with a *C. pubescens* plant or a *C. pubescens* hybrid to produce one or more plants of a second cross; and (i) crossing one or more plants of the second cross with a *C. annuum* plant or *C. annuum* hybrid to produce one or more plants of a third cross, parts thereof or seeds therefrom.

Also included in the present invention is a method of producing plants of a first cross, second cross and third cross from plants of an interspecific F1 hybrid between *C. annuum* and *C. pubescens*. Methods of preparing plants of a first cross, second cross, and third cross can comprise:

(a) pollinating a male sterile flower of a *C. annuum* parent selected from a *C. annuum* plant or a *C. annuum* hybrid with pollen from a *C. pubescens* plant or *C. pubescens* hybrid to form a pollinated flower;

(b) following (a), treating the pollinated flower with an auxin compound;

(c) growing the *C. annuum* parent until the pollinated flower develops into a fruit bearing a seed;

(d) harvesting the fruit bearing a seed that develops from the pollinated flower;

(e) rescuing embryonic tissue from the seed of the fruit to produce an interspecific F1 hybrid pepper plant;

(f) preparing one or more plants of a first cross employing the interspecific F1 hybrid pepper plant of (e);

(g) selecting one or more plants of a first cross with pollen that is more fertile than that of the interspecific F1 hybrid, to produce one or more selected plants of a first cross;

(h) crossing the one or more selected plants of a first cross with a *C. pubescens* plant or a *C. pubescens* hybrid to produce one or more plants of a second cross; and (i) crossing one or more plants of the second cross with a *C. annuum* plant or *C. annuum* hybrid to produce one or more plants of a third cross, parts thereof or seeds therefrom.

Alternatively, methods of preparing plants of a first cross, second cross, and third cross from *C. annuum* and *C. pubescens* can comprise:

(a) culturing a flower bud of a *C. annuum* parent selected from a *C. annuum* plant or *C. annuum* hybrid to obtain a *C. annuum* flower;

(b) pollinating the *C. annuum* flower of (a) with pollen from a *C. pubescens* plant or a *C. pubescens* hybrid to form a pollinated flower;

(c) following the pollination in (b), removing and subculturing the ovaries from the pollinated flower in the presence of an auxin compound and a cytokinin compound;

(d) maintaining the subcultured ovaries until fruit bearing a seed develops;

(e) rescuing immature embryo tissue from the seed of the fruit to produce an interspecific F1 hybrid pepper plant;

(f) preparing one or more plants of a first cross employing the interspecific F1 hybrid pepper plant of (e);

(g) selecting one or more plants of a first cross with pollen that is more fertile than that of the interspecific F1 hybrid, to produce one or more selected plants of a first cross;

(h) crossing the one or more selected plants of a first cross with a *C. pubescens* plant or a *C. pubescens* hybrid to produce one or more plants of a second cross; and (i) crossing one or more plants of the second cross with a *C. annuum* plant or *C. annuum* hybrid to produce one or more plants of a third cross, parts thereof such as seeds therefrom.

Plants of a subsequent cross, which are also within the scope of the present invention, may be prepared from plants of a third cross by crossing a plant of a third cross one or more times with a *C. annuum* plant, *C. annuum* hybrid or a member of the *Capsicum* genus that is not *C. annuum* to prepare plants of a subsequent cross.

The present invention also includes and provides for a method of preparing hybrid between *C. annuum* and *C. pubescens* using a bridging species comprising:

(a) performing a first cross between a *C. annuum* plant or a *C. annuum* hybrid and a plant of a bridging *Capsicum* species selected from the group consisting of: *C. chinense, C. baccatum, C. praetermissum*, and *C. eximium* to form a *C. annuum* hybrid, and crossing one or more progeny from the first cross with a *C. pubescens* plant to form the hybrid between *C. annuum* and *C. pubescens*.

In one aspect, the present invention includes methods of preparing an interspecific F1 hybrid pepper plant, plant of a first cross, plant of a second cross, plant of a third cross, plants of a subsequent cross, and plants prepared by bridge crosses, where the plants are not a progeny of a member of the *Capsicum* genus selected from *C. eximium, C. tovarii* and *C. cardenasii* and have no nuclear genetic material unique to one or more of *C. eximium, C. tovarii* or *C. cardenasii*.

The present invention includes and provides for plants produced by the methods of the present invention, parts of those plants, such as seeds thereof. In one aspect, the present invention is directed to a *C. annuum* hybrid bearing one or more introgressions from *C. pubescens*, where said plant is not the progeny of a plant of a *Capsicum* species selected from *C. cardenasii, C. eximium*, and *C. tovarri*. Such plants have no nuclear genetic material (DNA) unique to one or more of *C. eximium, C. tovarri* and *C. cardenasii*.

Also included and provided in the present invention are tissue cultures, comprising cells or protoplasts of the plants produced by the methods of the present invention. The cell and protoplasts may be a cell or protoplast taken from a tissue selected from the group consisting of leaves, pollen, embryos, roots, root tips, anthers, flowers, fruit, and seeds.

Another aspect of the present invention is directed to improving the ability to cross the progeny of an interspecific F1 hybrid pepper plant with other members of the *Capsicum* genus and obtain viable progeny, non-sterile progeny, or combinations of either. By improving the ability to prepare crosses, the ability to introgress traits into *Capsicum* species different from the species in which they originate is improved. In one aspect, improvements may be achieved by preparing plants of a first cross, second cross, third cross, or plants of a subsequent cross.

DETAILED DESCRIPTION OF THE INVENTION

The ability of plant breeders to introgress traits from other species of the same genus into cultivated species can result in crops with improved traits, including improved resistance to pathogenic organisms. As with many other species, however, a variety of barriers to the preparation of crosses between *C. annuum* and other members of the *Capsicum* genus such as *C. pubescens* exist. It has even been suggested that *C. annuum* and *C. pubescens* are the most remote and incompatible of the *Capsicum* genus. See Molkhova E. and Mikhailova M., *Interspecific hybridization among the species Capsicum annuum, Capsicum pendulum and capsicum Pubescens*, in Otdalechena khibridizatsiia pri rasteniiata: materiali ot Simpozium po otdalechena khibridizatsiia s mezhdunarodno uchs\astie, Sofia 14-15 IX (1982), published by Izd-vo na Bulgarskata akademiia na naukite, 1983, Sofia.

Some investigators have examined the potential for preparing crosses between *C. annuum* and *C. pubescens* and determined that the species can hybridize only in one direction, with *C. annuum* serving as the female. See Onus A. N., et al., *Unilateral Incompatibility in Capsicum (Solanaceae): Occurrence and Taxonomic Distribution*, Annals of Botany 94: 289-295 (2004). It has been reported that plants resulting from crosses between *C. annuum* and *C. pubescens* are sterile. See Walsh B. M. and Hoot S. B., *Phylogenetic Relationships of Capsicum (Solanaceae) using DNA Sequences from Two Noncoding Regions: the Chloroplast atpB-rbcl Spacer Region and Nuclear waxy Introns*, Int. J. Plant Sci. 162(6) 1409-1418 (2001) at FIG. 2.

Figure 1:
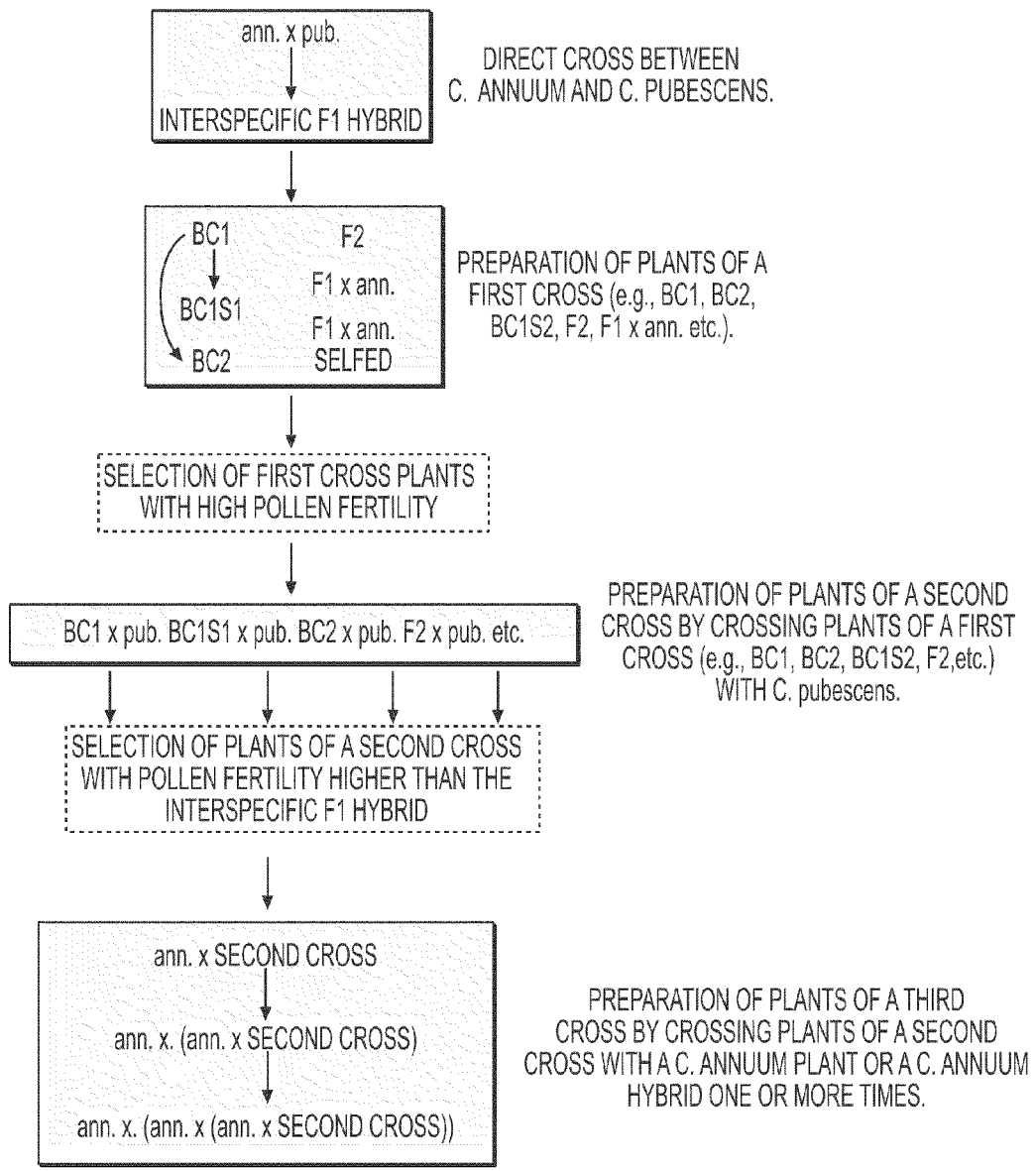
FIG. 1 shows Scheme 1 providing exemplary strategies for the preparation of direct crosses between *C. annuum* and *C. pubescens* to produce an F1 generation (interspecific F1 hybrid), and the development of progeny from the F1 generation.

The present application describes and provides methods to produce direct and indirect (e.g., bridge) crosses between members of the cultivated pepper species *C. annuum* and another member of the *Capsicum* genus, *C. pubescens*. In some aspects, the methods, or parts of the methods, are conducted in vivo and, in other aspects the methods, or parts of the method, are conducted in vitro. The instant application further describes and provides for methods of preparing plants (and their seeds) and populations of plants derived from interspecific F1 hybrids of *C. annuum* and *C. pubescens* that have a variety of traits including improved pollen fertility (see e.g., plants of a second cross in Scheme 1 as depicted in FIG. 1). Improved pollen fertility simplifies the generation of suitable numbers of progeny in subsequent crosses thereby facilitating selection of introgressed traits. Improved polled fertility refers to an increased percentage of fertile pollen with respect to the non-improved parent strain. Where the pollen of the parent plant has low fertility, any increase in pollen fertility is considered an increased percentage of fertile pollen. Overall pollen fertility may increase 0.005%, 0.007%, 0.01%, 0.1%, 0.2%, 0.3%, 0.5%, 0.6%, 0.7%, 0.8% 0.9%, 1.0%, 1.5%, or more over non-improved parent strain. Pollen fertility may be increased to about 5%, about 10%, about 15%, about 20%, or 25% or more over non-improved parent strain. Overall pollen fertility may increase from 0.001% to 0.01%, from 0.005% to 0.01%, from 0.005% to 0.1%, from 0.005% to 0.2%, from 0.005% to 0.3%, from 0.005% to 0.5%, from 0.005% to 0.6%, from 0.005% to 0.7%, from 0.005% to 1.0%, and from 0.005% to 1.5%%. In other aspects, pollen fertility may be increased to 30%, 40%, 50%, 60%, 75%, 85% or more over non-improved parent strain. In a preferred aspect, pollen fertility may be 90% or more over non-improved parent strain. In a more preferred aspect pollen fertility may be 95% or more over non-improved parent strain. In a most preferred aspect, pollen fertility may be 100% over non-improved parent strain. Pollen fertility may be determined by assessing the number of rounded pollen grains that are well stained by the chromosome stain acetocarmine. Rounded pollen represents normal pollen and serves as a surrogate measure of viable pollen, but the measure is not necessarily equal to viable pollen. Also described and provided for are methods for introducing *C. pubescens* traits and nuclear genetic material (nucleic acid molecules) into *C. annuum* by bridge crossings, where a *C. pubescens* or *C. annuum* plant is first crossed with another species of the *Capsicum* genus and the resulting hybrid is employed in subsequent crosses.

Among the traits that can be introgressed from *C. pubescens* into *C. annuum* are geminivirus resistance, tobamovirus resistance, *Xanthomonas* resistance, ease of fruit shedding, cold tolerance, leaf hair, purple flower, purple style, purple anther filament, leaf wrinkle, black seeds, fruit color, fruit type, thick fruit walls, flavor differences, and the clustering of seed-bearing placental tissue close to the stem of the fruit. In one aspect, the trait selected is geminivirus resistance, tobamovirus resistance, *Xanthomonas* resistance or resistance to a combination thereof.

As seeds of *Capsicum* species including *C. annuum* are cream colored, (see Walsh B. M. and Hoot S. B., Int. J. Plant Sci. 162(6) 1409-1418 (2001)), the ability to prepare black seeded *C. annuum* hybrids also permits a means of easily identifying the seeds, their source, and products made from those seeds or pepper fruit including those seeds (e.g., chili powder).

Exemplary strategies for the preparation of direct crosses between *C. annuum* and *C. pubescens* to produce an F1 generation (interspecific F1 hybrid), and the development of progeny from the F1 generation, denoted plants of the first cross, are shown in Scheme 1 as depicted in FIG. 1. Scheme 1 as depicted in FIG. 1, includes the development of progenies with improved pollen fertility from plants of a first cross, plants of a second cross, or both. Also provided for in Scheme 1 depicted in FIG. 1 is the use of plants of a second cross in subsequent crosses with a *C. annuum* hybrid or a *C. annuum* plant to produce plants of a third cross and plants of a subsequent cross.

Figure 2:
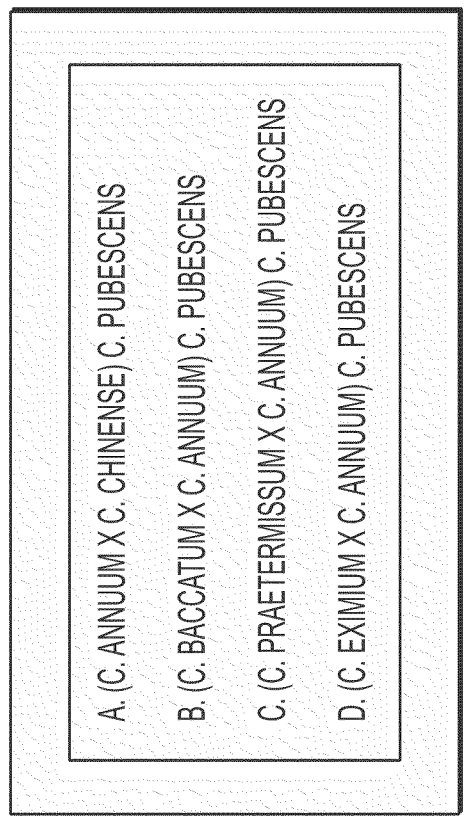
FIG. 2 shows Scheme 2 outlining bridge crossings, to introduce *C. pubescens*' traits and nucleic acid molecules into *C. annuum*.

Bridge crossings, to introduce *C. pubescens*' traits and nucleic acid molecules into *C. annuum* are outlined in Scheme 2 as depicted in FIG. 2. The bridge crosses can be accomplished by first crossing *C. pubescens* or *C. annuum* with one other species of the *Capsicum* genus to form hybrids, and subsequently crossing the hybrid as generically outlined for five different crosses (a through e) in Scheme 2 depicted in FIG. 2. Hybrids are first formed between plants of the type listed in parentheses, and the hybrid is subsequently crossed with the remaining plant type.

Bridge crosses advantageously permit the incorporation of traits of multiple pepper species into a single pepper hybrid. For example, disease resistance to multiple organisms can be introgressed into *C. annuum* from two or more non-*C. annuum* species using bridge crosses.

Also included in the instant application are hybrids of *C. annuum* and *C. pubescens* plants, parts thereof, tissue cultures of cells or protoplasts prepared from one or more tissues of such plants, parts of such plants, and seeds for such plants.

Definitions

A "*C. annuum* plant" is a plant of the genus *Capsicum* and of the species *annuum*.

A "*C. annuum* hybrid" is a *C. annuum* plant having one or more segments of nuclear DNA introgressed from another member of the *Capsicum* genus, where greater than about 50%, 60%, 75% of the nuclear DNA is DNA derived from a *C. annuum* plant. In some aspects, a *C. annuum* hybrid has greater than 80%, 85%, 90%, 95%, 98% or 99% of its nuclear DNA derived from a *C. annuum* plant. In some aspects the introgressions found in a *C. annuum* hybrid are introgressions from one or more *Capsicum* species selected from the group consisting of *C. chinense, C. baccatum, C. praetermissum, C.*

*frutescens, C. galapagoense,* and *C. eximium.* In other aspects, the introgressions found in a *C. annuum* hybrid are introgressions from one or more *Capsicum* species selected from the group consisting of *C. chinense, C. baccatum, C. praetennissum,* and *C. eximium.* In other aspects, the introgressions found in a *C. annuum* hybrid are introgressions from one or more *Capsicum* species selected from the group consisting of *C. chinense, C. frutescens,* and *C. praetermissum.* In another aspect the introgressions found in a *C. annuum* hybrid are introgressions from *C. annuum, C. baccatum,* or both *C. annuum* and *C. baccatum.* In another aspect, a *C. annuum* hybrid has no nuclear genetic material derived from *C. eximium, C. tovarii* or *C. cardenasii* that is unique to a purple flowered member of the *Capsicum* genus. In another aspect, a *C. annuum* hybrid has no nuclear genetic material specific or unique to one or more of *C. eximium, C. tovarii* or *C. cardenasii* plants.

A "*C. pubescens* plant" is a plant of the genus *Capsicum* and of the species *pubescens.*

A "*C. pubescens* hybrid" is a *C. pubescens* plant having one or more segments of nuclear DNA introgressed from another member of the *Capsicum* genus, where greater than about 75% of the nuclear DNA is DNA derived from a *C. pubescens* plant. In some aspects, a *C. pubescens* hybrid has greater than 80%, 85%, 90%, 95%, 98% or 99% of its nuclear DNA derived from a *C. pubescens* plant. In another aspect, a *C. pubescens* hybrid has no nuclear genetic material derived from *C. eximium, C. tovarii* or *C. cardenasii* that is unique to a purple flowered member of the *Capsicum* genus. In another aspect, a *C. pubescens* hybrid has no nuclear genetic material specific or unique to one or more of *C. eximium, C. tovarii* or *C. cardenasii* plants.

In one aspect, a plant of a first cross or plants of a first cross refers to a plant or plants having an interspecific F1 hybrid of *C. annuum* and *C. pubescens* as an immediate parent or grandparent, where a plant is not derived by crossing an interspecific F1 hybrid with a *C. pubescens* parent of an interspecific F1 hybrid. In another aspect, a plant of a first cross or plants of a first cross means a plant or plants having an interspecific F1 hybrid of *C. annuum* and *C. pubescens* as a great-grandparent, where the plant is not derived by crossing the interspecific F1 hybrid with the *C. pubescens* parent of the interspecific F1 hybrid. In one aspect, plants of a first cross include progeny of an interspecific F1 hybrid of *C. annuum* and *C. pubescens* that have been produced by crossing an interspecific F1 hybrid back to its *C. annuum* parent once (BC1) or twice (BC2), and plants produced by selfing a BC1 plant (BC1S1 plants). In other aspects, a plant of a first cross or plants of a first cross include plants produced by: selfing an interspecific F1 hybrid of *C. annuum* and *C. pubescens* (F2 plants); crossing an interspecific F1 hybrid of *C. annuum* and *C. pubescens* once or twice with a *C. annuum* plant or a *C. annuum* hybrid that is not a parent of the interspecific F1 hybrid; or crossing an interspecific F1 hybrid of *C. annuum* and *C. pubescens* once with a *C. annuum* plant or a *C. annuum* hybrid that is not a parent of a interspecific F1 hybrid to produce a progeny that is subsequently selfed.

A plant of a second cross or plants of a second cross refers to the progeny of a cross between a plant of a first cross and a *C. pubescens* plant or *C. pubescens* hybrid.

A plant of a third cross or plants of a third cross refers to the progeny of a cross between a plant of a second cross and a *C. annuum* plant or *C. annuum* hybrid.

Plants produced in subsequent crosses of a plant of a third cross, even where members of the *Capsicum* genus other than *C. annuum* are employed, are referred to as plants of a subsequent cross.

As used herein an "auxin compound" is indole-3-acetic acid (IAA), or a compound that can be substituted for it that is capable of variety of growth phenomena controlled by auxin including for example, inducing plant cell enlargement. In one aspect, an auxin compound may induce cell enlargement which may be increase in the size of a cell 5%, 10%, 15%, 20% or more relative to the untreated cell. In another aspect, an auxin compound may initiate cell division. In another aspect an auxin compound may regulate cell and organ differentiation. See, N. P Kefford, P. L Goldacre, *The Changing Concept of Auxin,* 48 American Journal of Botany 643, 643-650 (1961). Auxin compounds include, but are not limited to, one or more of: indole-3-acetic acid; naphthalene acetic acid (NAA); indole butyric acid (IBA); picloram, dicamba; gibberellin (GA3); and 2,4-dichlorophenoxy acetic acid (2,4-D). An auxin compound also includes compositions comprising one or more of the above-mentioned compounds and compositions comprising a combination of two or more of the above-mentioned compounds.

In some aspects of the methods of the present invention, an auxin compound is selected from the group consisting of: indole-3-acetic acid (IAA); naphthalene acetic acid (NAA); indole butyric acid (IBA); picloram, dicamba; gibberellin (GA3); and 2,4-dichlorophenoxy acetic acid (2,4-D). In other aspects, ubiquitin and brassinolide can be employed as an auxin compound. In still other aspects, an auxin compound is naphthalene acetic acid or a composition comprising naphthalene acetic acid. In still other aspects, an auxin compound can be applied in combination with a cytokinin; for example an auxin compound can comprise a combination of NAA, IBA or IAA, and a cytokinin compound.

As used herein a "cytokinin compound" or "kinin" is benzyladenine (also known as BA, 6-BA, 6-benzylaminopurine, BAP, or 6-benzyladenine) or a compound that can be substituted for it that is capable of inducing plant shoot formation. Cytokinin compounds include, but are not limited to, one or more of: benzyladenine; 6-benzylaminopurine riboside; 1-phenyl-3-(1,2,3-thiadiazol-5-yl)urea; 6-(γ,γ-dimethylallylamino)purine; DL-Dihydrozeatin; t-zeatin riboside; zeatin; N-(2-chloro-4-pyridyl)-N'-phenylurea; N-benzyl-9-(2-tetrahydropyranyl)adenine; kinetin; kinetin riboside; and isopentyladenosine. A cytokinin compound also includes compositions comprising one or more of the above-mentioned compounds and compositions comprising a combination of two or more of the above-mentioned compounds.

In some aspects of the methods, a cytokinin compound is selected from the group consisting of: 6-benzyladenine; 6-benzylaminopurine riboside; 1-phenyl-3-(1,2,3-thiadiazol-5-yl)urea; 6-(γ-γ-dimethylallylamino)purine; DL-dihydrozeatin; t-zeatin riboside; zeatin; N-(2-chloro-4-pyridyl)-N'-phenylurea; N-benzyl-9-(2-tetrahydropyranyl)adenine; kinetin; kinetin riboside; isopentyladenosine and combinations of two or more thereof. In other aspects, a cytokinin compound is 6-benzyladenine or a composition comprising 6-benzyladenine. In still other aspects, a cytokinin is a composition comprising 6-benzyladenine and another cytokinin compound.

"Part(s) of a plant" or a "plant part(s)" includes, without limitation, leaves, calyx, pollen, embryos, pedicle, peduncle, cotyledon, hypocotyl, meristematic cells, roots, root tips, anthers, flowers, seeds, stem, and pepper fruit.

Pepper fruit may be referred to as sweet, mild, medium, hot or very hot pepper varieties. As used herein those terms are defined as follows:

A "sweet" pepper is a pepper fruit having about 0 Scoville Heat Units (SHU) or less than about 0.5 ppm (parts per million) which is less than about 7 SHU of total capsaicins (capsaicin, norhydrocapsaicin, and dihydrocapsaicin).

A "mild" pepper is a pepper fruit having greater than about 0.5 ppm (greater than about 7.5 SHU) to about 4.0 ppm (60 SHU) of total capsaicins, or more preferably about 2 ppm (30 SHU ) to 3 ppm (45 SHU) of total capsaicins based upon the weight and capsaicin content of whole pepper fruit.

A "medium" pepper is a pepper fruit having greater than about 4 ppm (greater than about 60 SHU) to about 10 ppm (150 SHU) of total capsaicins, or more preferably about 5 ppm (105 SHU ) to 9 ppm (135 SHU) of total capsaicins.

A "hot" pepper is a pepper fruit having greater than about 10 ppm (greater than about 150 SHU) to about 19 ppm (about 285 SHU) of total capsaicins, or more preferably greater than about 14 ppm (210 SHU) of total capsaicins.

A "very hot" or "extra hot pepper" is a pepper fruit having greater than about 19 ppm (greater than about 285 SHU) or more preferably about 20 ppm (about 300 SHU) of total capsaicins. Very hot peppers or extra hot peppers include peppers with 20 ppm to 100 ppm, 100 ppm to 200 ppm, and 200 ppm to about 500 ppm of total capsaicins.

Capsaicin content or SHU units can be determined by methods known in the art including HPLC methods as described for example in Garces-Claver et al., *Determination of Capsaicin and Dihydrocapsaicin in Capsicum Fruit by Liquid Chromatography—Electrospray/Time-of-Flight Mass Spectrometry*, J. Agric. Food Chem. 54: 9303-9311 (2006), hereby incorporated by reference in its entirety. A skilled artisan will understand that capsaicin levels can vary, and that the capsaicin content of some pepper fruit tissues (e.g., placenta) can be higher than that of other tissues. See, Sung et al., *Capsaicin biosynthesis in water-stressed hot pepper fruits*, Bot. Bull. Acad. Sin. 46: 35-42 (2005), hereby incorporated by reference in its entirety.

In an aspect of the present invention, "a pepper plant having a specified trait" is a pepper plant having one or more traits selected from the group consisting of:
  a. plants with prostrate, compact, erect growth habits;
  b. plants that have glabrous stems or have sparse, intermediate or abundant stem pubescens;
  c. plants that are glabrous leaves or have sparse, intermediate or abundant leaf pubescens;
  d. plants with green or purple stems;
  e. plants that have pendant, intermediate, or erect pedicle position at anthesis;
  f. plants that have white, green-white, lavender, blue or violet corolla color;
  g. plants with yellow, pale blue, blue, or purple anthers;
  h. plants with white or blue filament colors;
  i. plants having a stigma included within the anthers, at the same level as the anthers, or exerted beyond the anthers at full anthesis;
  j. plants that are male sterile or male fertile;
  k. plants that have low, intermediate or high fruit set;
  l. plants with white, straw or cream, yellow, brown, dark brown, or black seeds;
  m. plants that have smooth, intermediate, or dentate calyx margins;
  n. plants that have or lack an annular constriction at the junction of the calyx and peduncle;
  o. plants that have declining, intermediate, or erect fruit position;
  p. plants that have green, yellow, orange, red, purple, brown, or black immature fruit;
  q. plants that have green, yellow, orange, red, purple, brown, or black mature fruit;
  r. plants with pepper fruit that is sweet, or has low (i.e. mild), intermediate (i.e. medium) or high (i.e. hot or very hot) pungency;
  s. plants that have an average fruit length at ripeness that is very short (less than about one cm), short (about 5 cm or about 2 to about 7 cm), medium (about 10 cm or about 7 to about 12 cm), long (about 15 cm or about 13 to about 25 cm) or very long (greater than 25 cm or about 25 cm to about 40 cm);
  t. plants with a fruit wall thickness (measured halfway between the point of attachment of the stem and the blossom end) from about 0.5 to 1.5 mm or from about 1 to about 2.5 mm or from about 1.5 to about 4 mm or from about 2 to about 5 mm, or from about 3 to about 6 mm, or from about 3.5 mm to about 7.5 mm;
  u. plants that have an average fruit width at ripeness that is about 0.3 to 1 cm, about 1 to 2 cm, about 2 to 4 cm, about 3 to 7, about 6 to 10, about 7 to 11 or greater than about 11 cm;
  v. plants without persistent fruit or plants with persistent fruit (fruit that persists and maintains an attachment to the plant after ripening);
  w. plants with pepper fruit having an average weight a ripeness from about 1 to 5 g, 5 to 25 g, 25 to 50 g, 50 to 100 g, 100 to 250 g, 150 to 450 g, 200 to 500 g or 300 to 550 g.
  x. plants with pepper fruit that is elongate, oblate, round, conical or pointed, campanulate, or bell/blocky;
  y. plants where the pepper fruit shape at the point of attachment is acute, obtuse, truncate, cordate, or lobate;
  z. plants where the pepper fruit has or lacks a neck at the base of the fruit;
  aa. plants where the blossom end is pointed, blunt, or sunken;
  bb. plants where the pepper fruit has a smooth, slightly corrugated, intermediate, or very corrugated cross section;
  cc. plants with resistance to one or more insect pests (e.g., nematodes and aphids);
  dd. plants with resistance to diseases caused by one or more bacteria or fingi (e.g., *xanthamonas* sp. and *Leveillula taurica*);
  ee. plants with resistance to diseases caused by one or more viruses (e.g., geminivirus, tobamovirus);
  ff. plants having or lacking anthocyanins in unripe pepper fruit;
  gg. plants having or lacking anthocyanins in ripe pepper fruit;
  hh. plants that are resistant or susceptible to low temperature;
  ii. plants that are resistant or susceptible to high temperature;
  jj. plants that are resistant or susceptible to drought;
  kk. plants that are resistant or susceptible to high soil moisture;
  ll. plants that are resistant or susceptible to high humidity; and
  mm. plants that shed fruit easily or do not shed fruit easily.

In an aspect of the present invention, "a pepper plant of a named variety" is a pepper plant of a variety selected from the group consisting of: Aleppo, Anaheim, ancho, bell, cascabel, cayenne, chilaca, chiltepin, cubanelle, de arbol, dandicut, Fresno, guajillo, Hungarian wax, Italian sweet, jalapeño, Japanese, mirasol, macho, mulato, New Mexico, pasilla, pepperoncini (Tuscan), piquin, pimento, poblano, puya, Serrano and Tientsin (Tien Tsin) pepper varieties.

Direct Crosses Between *C. annuum* and *C. pubescens*

Despite the barriers to crossing *C. annuum* and *C. pubescens* that result in the abortion of most flowers shortly after pollination, *C. annuum* and *C. pubescens* can be directly crossed to produce F1 progeny using protocols involving steps that are conducted in vitro, in vivo, or a combination thereof.

Crosses between *C. annuum* and *C. pubescens* to produce interspecific F1 hybrid pepper plants can be accomplished for example by:

(a) pollinating a male sterile flower of a *C annuum* parent selected from a *C. annuum* plant or a *C. annuum* hybrid with pollen from a *C. pubescens* plant or *C. pubescens* hybrid to form a pollinated flower;

(b) following (a), treating the pollinated flower with an auxin compound;

(c) growing the *C. annuum* parent until the pollinated flower develops into a fruit bearing a seed;

(d) harvesting the fruit bearing a seed that develops from the pollinated flower; and (e) rescuing embryonic tissue from the seed of the fruit to produce an interspecific F1 hybrid pepper plant.

In one aspect, treating the pollinated flower with an auxin compound can be conducted the day following the pollinating of a male sterile flower of a *C. annuum* plant with pollen from a *C. pubescens* plant to form a pollinated flower. In some aspects treating the pollinated flower with an auxin compound can be conducted at time periods from about 16 to about 32 hours, or from about 18 to about 28 hours, or from about 20 to about 24 hours.

Methods can further include repollinating the pollinated flower with pollen from a *C. pubescens* plant or hybrid after treating the flower with an auxin compound in (b). Where the flower is treated with an aqueous solution of an auxin compound, repollinating can be conducted after the auxin solution has dried. In some aspects repollinating is conducted up to 1, 2, 4, 6, or 8 hours after the auxin solution has dried.

One other aspect of a method of the present invention includes a male sterile flower. In some aspects, the male sterile flower is sterile due to emasculation. Alternatively, the male sterile flower can be the flower of a genetically male sterile plant. In particular, the male sterility can be due to cytoplasmic male sterility resulting from the presence of allelic variations in the region of the cox II and atp6 loci (see Kim, D. H. and Kim B. D., Molecules and Cells, 20(3):416-22 (2005)). In particular, the open reading frame termed "orf456" found at the end of some *C. annuum* mitochondrial cox II genes may provide cytoplasmic male sterility (see Kim, D. H. et al., Plant Molecular Biology, 63(4):519-32 (2007)).

Crosses between *C. annuum* and *C. pubescens* to produce interspecific F1 hybrid pepper plants can also be accomplished employing in vitro method steps of the present invention, for example by:

(a) culturing a flower bud of a *C. annuum* parent selected from a *C. annuum* plant or *C. annuum* hybrid to obtain a *C. annuum* flower;

(b) pollinating the *C. annuum* flower of (a) with pollen from a *C. pubescens* plant or a *C. pubescens* hybrid to form a pollinated flower;

(c) following the pollination in (b), removing and subculturing the ovaries from the pollinated flower in the presence of an auxin compound and a cytokinin compound;

(d) maintaining the subcultured ovaries until fruit bearing a seed develops; and (e) rescuing immature embryo tissue from the seed of the fruit to produce an interspecific F1 hybrid pepper plant.

In some aspects, the flower buds are cultured for 10 to 36 hours under continuous illumination prior to pollinating the *C. annuum* flower, with pollen from a *C. pubescens* plant or hybrid to form a pollinated flower. In other aspects, the flower buds can be cultured under continuous illumination for about 10 to about 20 hours, or from about 14 to about 24 hours, or from about 16 to about 30 hours prior to the pollinating.

In another aspect, the *C. annuum* flowers are cultured under continuous illumination for from about 10 to about 36 hours following the pollinating of the *C. annuum* flower with pollen from a *C. pubescens* plant or hybrid to form a pollinated flower. In other aspects, the *C. annuum* flower buds can be cultured under continuous illumination for from about 12 to about 20 hours, or from about 14 to about 24 hours, or from about 16 to about 30 hours following the pollinating of the *C. annuum* flower with pollen from a *C. pubescens* plant to form a pollinated flower.

The concentration of an auxin compound that is employed to produce the desired effect, for example increasing the size of a cell or thereby maintaining the viability of a cell will vary depending on the compound or compounds employed and the means by which it is delivered. Typically, an auxin compound will be applied to plants or plant parts in an aqueous solution or suspension at a concentration from about 0.02 to about 0.4 g/l, or from about 0.05 to about 0.3 g/l, or from about 0.1 to about 0.25 g/l, or at about 0.2 g/l for application to flowers in vivo. Where an auxin compound is applied in vitro under conditions where a tissue is exposed to the compound for periods of 4 or more, or 8 or more, hours, the auxin compound can be applied to plants or plant parts in an aqueous solution or an aqueous suspension (e.g. in culture media) at a concentration from about 0.001 to about 0.4 mg/l, or from about 0.01 to about 0.2 mg/l or from about 0.05 to about 0.1 mg/l, or at about 0.05 mg/l.

The concentration of a cytokinin compound that is employed to produce the desired effect, for example increasing the size of a cell or thereby maintaining the viability of a cell, can be determined. The concentration can vary depending on the compound or composition employed and the means by which it is delivered. Typically, a cytokinin compound will be applied to plants or plant parts in an aqueous solutions or suspension. Where a cytokinin compound is applied in vitro under conditions where a tissue or cells are exposed to the compound for periods of 4 or more, or 8 or more, hours, a cytokinin compound can be applied in an aqueous solution or an aqueous suspension (e.g. in culture media) at a concentration from about 0.01 to about 0.8 g/l, or from about 0.05 to about 0.4 g/l or from about 0.1 to about 0.3 g/l, or at about 0.2 g/l.

In addition to the use of *C. annuum* plants as the female parent for the production of interspecific F1 hybrid pepper plants, *C. annuum* hybrids may be employed in an aspect. *C. annuum* hybrids that may be employed include *C. annuum* hybrids that have a desirable trait introgressed from another *Capsicum* species. Such a trait includes resistance to disease (bacterial, fungal, or viral) and pests (e.g. insects such as aphids or nematodes). The *C. annuum* hybrids may be employed also include a pepper plant having a specified trait. To avoid repetition, reference is made with respect to the traits of pepper plants (a) through (mm) to the full extent to the corresponding details provided above which apply equally to the specified trait. The *C. annuum* hybrids that may be employed may also be hybrids having introgressions from one or more *Capsicum* species selected from the group consisting of *C. baccatum, C. chacoense, C. chinense, C. frutescens, C. galapagoense,* and *C. praetermissum*. In another aspect a *C. annuum* hybrid of the present invention may be a hybrid having an introgression from one or more *Capsicum* species selected from the group consisting of *C. baccatum, C. chacoense, C. chinense*, and *C. frutescens*.

In one aspect, a *C. annuum* hybrid employed in preparing interspecific F1 hybrid pepper plants is not the progeny of a plant of a *Capsicum* species selected from *C. cardenasii, C. eximium*, and *C. tovarii*. Such plants have no nuclear DNA unique to one or more plants selected from *C. cardenasii, C. eximium*, and *C. tovarii*.

Progeny of Direct Crosses Between *C. annuum* and *C. pubescens*

Although interspecific F1 hybrid pepper plants produced by crossing *C. annuum* and *C. pubescens* can suffer from low pollen fertility (see, for example, Scheme 1 as depicted in FIG. 1 and Table 1), they can be used to prepare progeny by cross or selfing. Interspecific F1 hybrid pepper plants can be bred to produce F2, F3, F4 and subsequent progeny generations, or seeds for those plants. The present invention includes and provides for a seed that when grown produces an interspecific F1 hybrid pepper plant resulting from crossing *C. annuum* and *C. pubescens*. In addition, included and provided for are seeds that when grown produce an F2, F3, or F4 progeny of the interspecific F1 hybrid of *C. annuum* and *C. pubescens*.

The present invention includes and provides for parts, tissues, or cells of an interspecific F1 hybrid pepper plant or its F2, F3, F4 or subsequent filial progeny. In one aspect, the parts of a F1, F2, F3 or F4 progeny of an interspecific F1 hybrid of *C. annuum* and *C. pubescens* are selected from the group consisting of leaves, pollen, embryos, cotyledon, hypocotyl, meristematic cells, roots, root tips, anthers, flowers, seeds, stem, and pepper fruit. Cells of the interspecific F1 hybrid plant, or its F2, F3 or F4 progeny, may be present as a tissue culture produced from cells or protoplasts of a tissue selected from the group consisting of: leaves, pollen, embryos, cotyledon, hypocotyl, meristematic cells, roots, root tips, anthers, flowers, seeds, stem, and pepper fruit.

In addition, the interspecific F1 hybrids of *C. annuum* and *C. pubescens*, or their F2, F3, F4, or subsequent progeny, can be crossed with other members of the *Capsicum* genus including, but not limited to, one or more of *C. annuum, C. baccatum, C. cardenasii, C. chacoense, C. chinense, C. ciliatum, C. eximium, C. flexuosum, C. frutescens, C. galapagoense, C. praetermissum, C. pubescens*, and *C. tovarii*. The invention includes and provides for plants and parts of plants produced by such crosses, and seeds to produce plants of such crosses.

In some aspects, progeny of F1 interspecific hybrid pepper plants are not also progeny of another purple flowered member of the *Capsicum* genus. In one aspect, progeny of F1 interspecific hybrid pepper plants are not the progeny of a member of the *Capsicum* genus selected from *C. eximium, C. tovarii* or *C. cardenasii*. Such progeny plants have no nuclear genetic material unique to one or more of *C. eximium, C. tovarii* or *C. cardenasii*.

One aspect of the present invention provides for and includes plants produced by crossing an interspecific F1 hybrid of *C. annuum* and *C. pubescens*, or its F2 or F3 progeny, one or more times with plants independently selected from those of the *Capsicum* genus and the species: *annuum, cardenasii, chinense, eximium, frutescens, praetermissum*, and *pubescens*, or a *C. annuum* hybrid. The present invention includes and provides for plants and parts of plants produced by such crosses, and seeds to produce plants of such crosses.

In another aspect, the present invention provides for and includes plants produced by crossing an interspecific F1 hybrid of *C. annuum* and *C. pubescens*, or its F2 or F3 progeny, one or more times with plants independently selected from those of the *Capsicum* genus and the species: *annuum, chinense, frutescens, praetermissum*, or a *C. annuum* hybrid. The present invention includes and provides for plants and parts of plants produced by such crosses, and seeds to produce plants of such crosses.

In another aspect, the present invention provides for and includes plants produced by crossing an interspecific F1 hybrid of *C. annuum* and *C. pubescens*, or its F2, F3 or F4 progeny, one or more times with an independently selected *C. annuum* plant or a *C. annuum* hybrid. The present invention includes and provides for plants and parts of plants produced by such crosses, and seeds to produce plants of such crosses.

In addition to including and providing for interspecific F1 hybrids between *C. annuum* and *C. pubescens*, the present invention includes and provides for plants produced by backcrossing of the interspecific F1 hybrid to its *C. annuum* parent, including multiple back crosses to the *C. annuum* parent as a recurrent parent, to form subsequent generations of plants (BC1, BC2, BC3, BC4, etc.). The present invention also includes and provides for plants and populations of plants that arise from selfing one or more plants produced from backcrosses of the F1 hybrid (e.g., BC1S1, BC1S2, BC2S1 or BC2S2). Crosses between *C. annuum* hybrids and interspecific F1 hybrids of *C. annuum* and *C. pubescens*, or subsequent filial generations are also included in the present invention.

The present invention also includes and provides for embryos, cells and tissue cultures of cells or protoplasts derived from the tissues of an interspecific F1 hybrid of *C. annuum* and *C. pubescens*, and its progeny. More specifically, the present invention includes and provides for embryos, cells and tissue cultures of cells or protoplasts derived from the tissues of plants produced by:

(a) backcrossing the interspecific F1 hybrid to a parent of the interspecific F1 hybrid (e.g., BC1, BC2, BC3, BC4, BC1S1, BC1S2, BC2S1 or BC2S2);

(b) crossing members of the same filial generation (e.g., F2, F3, F4); and (c) crossing one or more independently selected *C. annuum* plants or hybrids with an interspecific F1 hybrid of *C. annuum* and *C. pubescens* one or more times (e.g., ann.× F1, ann./(ann.×F1), ann.//ann./(ann.×F1), ann.×F2, ann./(ann.×F2), ann.//ann./(ann.×F2), ann.×F3, ann./(ann.×F3), or ann.// ann./(ann.×F3) ).

In one aspect, the present invention includes and provides for plants, including the progeny of interspecific F1 hybrid pepper plants (e.g., plants of a first, second, or third cross, or plants of a subsequent cross), where the plants do not have one or more plants of a *Capsicum* species selected from *C. cardenasii, C. eximium*, and *C. tovarii* as an ancestor. Such plants, which can be fertile (non-sterile), have no nuclear DNA specific or unique to one or more plants selected from *C. cardenasii, C. eximium*, and *C. tovarii*. Such a plant may be prepared by using ancestral plants that are not *C. cardenasii, C. eximium*, or *C. tovarii* or the progeny of *C. cardenasii, C eximium*, and *C. tovarii* (i.e., neither *C. annuum* hybrids nor *C. pubescens* hybrids have *C. cardenasii, C. eximium*, and *C. tovarii* as an ancestor). Also included in the scope of the present invention are parts of such plants, including their seeds and pepper fruit. Plants regenerated from embryos, cells, protoplasts, and tissue cultures of cells or protoplasts, having an F1 hybrid pepper plants produced by crossing *C. annuum* and *C. pubescens* as an ancestor are also within the scope of the present invention.

The progeny of interspecific F1 hybrid plants may be screened for traits derived from the *C. pubescens* plant or *C.*

*pubescens* hybrid that is employed as a parent of the F1 hybrid. In addition, traits introduced in subsequent crosses can also be selected. In one aspect, a plant is selected to have a trait selected from the group consisting of: geminivirus resistance, tobamovirus resistance, *Xanthomonas* resistance, ease of fruit shedding, cold tolerance, leaf hair, flower coloration (e.g., purple flower, purple style, purple anther filament), black seeds, fruit color, thick fruit walls, flavor differences, and the clustering of seed-bearing placental tissue close to the stem of the fruit.

In another aspect of the present invention the progeny are selected for introduction of diseases and pests resistance traits that affect members of the *Capsicum* genus, particularly *C. annuum*. Diseases that affect members of the *Capsicum* genus include viral, bacterial and fungal diseases.

Viruses that can affect members of the *Capsicum* genus include, but are not limited to, Alfalfa mosaic virus, Aster ringspot virus, cucumber mosaic virus, Curley-top virus, geminivirus including pepper huasteco geminivirus (PHV), pepper mottel virus, pepper mild mottel virus, potato virus Y, stolbur mosaic virus, tobacco etch virus, tobacco leaf curl virus, and tobamoviruses (including Tobacco mosaic virus).

Bacteria that can affect members of the *Capsicum* genus include, but are not limited to, *Pseudomonas syringae, Ralstonia solanacearum*, and *Xanthomonas*.

Fungi that can affect members of the *Capsicum* genus include, but are not limited to, *Alternaria solani, A. tenuis, Botrytis cinera, Cercospora capsici, Colletotrichum* sp. *Fusarium* sp., *Leveillula taurica, Mucor mucedo, Penicillium* sp., *Phytophtora capsisi* L., *P. citrophthora, Rhizoctonia solani, Rhizopus, Nigricans, Sclerotinia* sp., *Stemphylium botriosum, Stemphylium lycopersici*, and *Stemphylium solani* (Grey leaf spot).

Pests that can affect members of the *Capsicum* genus include, but are not limited to, *Anthonomus* sp. (weevil), *Aphis* sp. (e.g. *Myzus persicae* (Sulzer) (green peach aphid)), *Gnorimoschema* sp. (leaf miner), *Musue Pericae* (aphid), *Scirtothrips dorsalis* (thrip), *Spodoptera litura* (fruit borer), *Hemitarsonemus latus* (mite), Whiteflies, and *Meloidogyne* sp. (e.g., root-knot nematode). In one aspect, the trait of disease and pest resistance is selected from resistance to a geminivirus, tobamovirus resistance, *Xanthomonas*, aphids, and powdery mildew (*Leveillula taurica*).

Breeding and Selection of Interspecific F1 Hybrid Pepper Plant Progeny with Higher Pollen Fertility (1) Preparation of Interspecific F1 Hybrid Pepper Plant Progeny (Plants of a First Cross) with Increased Pollen Fertility Where it is desired to produce progeny of interspecific F1 hybrid pepper plants having improved ability to be crossed with other *Capsicum* plants (e.g., *C. annuum* plants or hybrids), or having higher pollen fertility than that of an interspecific F1 hybrid pepper plant, plants of a first cross may be prepared and selected for higher pollen fertility. To avoid repetitions, reference is made with respect to pollen fertility to the full extent to the corresponding details provided above which apply equally to pollen fertility described here. Hence, in addition to the steps for the production of the interspecific F1 hybrid pepper plants, methods of preparing the plants of a first cross can include steps for the preparation of progeny of the interspecific F1 hybrid pepper plant where the plant serves as parent, grandparent or great grandparent of the progeny, and subsequent selection of the progeny for pollen fertility. In one aspect, while plants of a first cross may be prepared by breeding the interspecific hybrid with itself, *C. annuum* plants or *C. annuum* hybrids (including the *C. annuum* parent of the interspecific F1 hybrid), neither *C. pubescens* plants nor *C. pubescens* hybrids are used in the preparation of plants of a first generation other than in the preparation of the interspecific F1 hybrid pepper plant itself.

In some aspects, where plants having higher pollen fertility are desired, an interspecific F1 hybrid pepper plant and its progeny will be prepared using only *C. annuum* plants as the *C. annuum* parent. In other aspects where plants having higher pollen fertility are desired, an interspecific F1 hybrid pepper plant and its progeny will be prepared using only *C. annuum* hybrids as the *C. annuum* parent. In other aspects, the interspecific F1 hybrid pepper plant and its progeny will be prepared using a *C. annuum* plant or hybrid as the *C. annuum* parent and a *C. pubescens* plant.

In one aspect, methods of preparing one or more plants of a first cross with pollen fertility higher than that observed in the interspecific F1 hybrid plant that served as the interspecific F1 hybrid parent, can comprise:

(1) preparing one or more plants of a first cross by crossing or selfing an interspecific F1 hybrid pepper plant one to three times with a *C. annuum* plant, a *C. annuum* hybrid, or a filial progeny of the interspecific F1 hybrid pepper plant (e.g., F2, F3 progeny) that has been independently selected for each crossing or selfing; and (2) selecting one or more plants of a first cross with pollen that is more fertile than that of the interspecific F1 hybrid.

Plants of the present invention can be selected for pollen fertility indirectly by assessing the number of rounded pollen grains that stain well with a chromosome stain such as acetocarmine. Alternatively, pollen can be tested for the ability to successfully pollinate the flowers of *C. annuum* plants or *C. annuum* hybrids. Improved pollen fertility refers to an increased percentage of fertile pollen with respect to the non-improved parent strain. Where the pollen of the parent plant has low fertility, any increase in pollen fertility is considered an increased percentage of fertile pollen. Overall pollen fertility may increase 0.005%, 0.007%, 0.01%, 0.1%, 0.2%, 0.3%, 0.5%, 0.6%, 0.7%, 0.8% 0.9%, 1.0%, 1.5%, or more over non-improved parent strain. Pollen fertility may be increased to about 5%, about 10%, about 15%, about 20%, or 25% or more over non-improved parent strain. Overall pollen fertility may increase from 0.001% to 0.01%, from 0.005% to 0.01%, from 0.005% to 0.1%, from 0.005% to 0.2%, from 0.005% to 0.3%, from 0.005% to 0.5%, from 0.005% to 0.6%, from 0.005% to 0.7%, from 0.005% to 1.0%, and from 0.005% to 1.5%%. In other aspects, pollen fertility may be increased to 30%, 40%, 50%, 60%, 75%, 85% or more over non-improved parent strain. Pollen fertility may be determined by assessing the number of rounded pollen grains that are well stained by the chromosome stain acetocarmine. Rounded pollen represents normal pollen and serves as a surrogate measure of viable pollen, but the measure is not necessarily equal to viable pollen.

In some methods of the present invention for preparing plants of a first cross with pollen fertility higher than that observed in the interspecific F1 hybrid plant that served as their parent, the interspecific F1 hybrid pepper plant and the plants of a first cross are prepared with *C. annuum* plants. In other methods, the interspecific F1 hybrid pepper plants and plants of a first cross are prepared with *C. annuum* hybrids.

In other aspects, methods of preparing one or more plants of a first cross with pollen fertility higher than that observed in the interspecific F1 hybrid plant that served as a parent, can comprise:

(1) preparing one or more plants of a first cross by:
  i) backcrossing an interspecific F1 hybrid pepper plant to the *C. annuum* parent of the interspecific F1 hybrid pepper plant one, two or three times to prepare one or more BC1, BC2, or BC3 plants, ii) backcrossing the interspecific F1 hybrid pepper plant to the *C. annuum* parent of the interspecific F1 hybrid pepper plant once or twice to prepare a BC1 or BC2 plant, and selfing the BC1 or BC2 plant once or twice to prepare one or more BC1S1, BC1S2, or BC2S1 plants;

iii) crossing members of the same filial generation derived from the interspecific F1 hybrid pepper plant to produce one or more F2, F3, or F4 plants; and iv) crossing one or more independently selected *C. annuum* plants or *C. annuum* hybrids with the interspecific F1 hybrid pepper plant one, two or three times (e.g., to produce a hybrid of the interspecific F1 hybrid pepper plant such as: ann.×F1, ann./(ann.×F1), ann.// ann./(ann.×F1), ann.×F2, ann./(ann.×F2), ann.// ann./(ann.×F2), ann.×F3 etc.); and (2) selecting one or more plants of a first cross with pollen that is more fertile than that of the interspecific F1 hybrid.

In other aspects, methods of preparing one or more plants of a first cross with pollen fertility higher than that observed in the interspecific F1 hybrid plant that served as a parent can comprise:

(1) preparing one or more plants of a first cross, where the plants of the first cross are BC1, BC2, BC2S1, BC1S1 or BC1S2 progeny of an interspecific F1 hybrid pepper plant prepared by:

i) preparing one or more BC1 plants by backcrossing the interspecific F1 hybrid pepper plant with its *C. annuum* parent, or with another *C. annuum* plant, to form one or more BC1 plants;

ii) preparing one or more BC2 progeny by backcrossing the interspecific F1 hybrid pepper plant with its *C. annuum* parent, or with another *C. annuum* plant, to form a BC1 plant, and backcrossing the BC1 plant with the *C. annuum* parent, or with another *C. annuum* plant, to form one or more BC2 plants;

iii) preparing one or more BC2S1 progeny by backcrossing the interspecific F1 hybrid pepper plant with its *C. annuum* parent, or with another *C. annuum* plant, to form a BC1 plant, and backcrossing the BC1 plant with the *C. annuum* parent, or with another *C. annuum* plant, to form a BC2 plant, and selfing the BC2 plant to form one or more BC2S1 plants;

iv) preparing one or more BC1S1 plants by backcrossing an interspecific F1 hybrid pepper plant with its *C. annuum* parent, or with another *C. annuum* plant, to form a BC1 progeny and selfing the BC1 progeny to form one or more BC1S1 plants; or v) preparing one or more BC1S2 plants by backcrossing an interspecific F1 hybrid pepper plant with its *C. annuum* parent, or with another *C. annuum* plant, to form a BC1 plant, selfing the BC1 plant to form one or more BC1S1 plants, and selfing the BCS1 plant to form one or more BC1S2 plants; and (2) selecting one or more plants of a first cross with pollen that is more fertile than that of the interspecific F1 hybrid.

In another aspect, methods of preparing one or more plants of a first cross with pollen fertility higher than that observed in the interspecific F1 hybrid plant that served as a parent can comprise:

(1) preparing BC1 plants by backcrossing the interspecific F1 hybrid pepper plant with its *C. annuum* parent, or with another *C. annuum* plant, to form the BC1 plants; and (2) selecting one or more BC1 plants with pollen that is more fertile than that of the interspecific F1 hybrid.

In another aspect, methods of preparing one or more plants of a first cross with pollen fertility higher than that observed in the interspecific F1 hybrid plant that served as a parent can comprise:

(1) preparing one or more BC2 progeny by backcrossing the interspecific F1 hybrid pepper plant with its *C. annuum* parent, or with another *C. annuum* plant, to form a BC1 plant, and backcrossing the BC1 plant with the *C. annuum* parent, or with another *C. annuum* plant, to form one or more BC2 plants; and (2) selecting one or more BC2 plants with pollen that is more fertile than that of the interspecific F1 hybrid.

In another aspect, methods of preparing one or more plants of a first cross with pollen fertility higher than that observed in the interspecific F1 hybrid plant that served as a parent, can comprise:

(1) preparing one or more BC2S1 progeny by backcrossing the interspecific F1 hybrid pepper plant with its *C. annuum* parent, or with another *C. annuum* plant, to form a BC1 plant, and backcrossing the BC1 plant with the *C. annuum* parent, or with another *C. annuum* plant, to form a BC2 plant, and selfing the BC2 plant to form one or more BC2S1 plants; and (2) selecting one or more BC2S1 plants with pollen that is more fertile than that of the interspecific F1 hybrid.

In another aspect, methods of preparing one or more plants of a first cross with pollen fertility higher than that observed in the interspecific F1 hybrid plant that served as a parent can comprise:

(1) preparing one or more BC1S1 plants by backcrossing an interspecific F1 hybrid pepper plant with its *C. annuum* parent, or with another *C. annuum* plant, to form a BC1 progeny and selfing the BC1 progeny to form one or more BC1S1 plants; and (2) selecting one or more BC1S1 plants with pollen that is more fertile than that of the interspecific F1 hybrid.

In another aspect, methods of preparing one or more plants of a first cross with pollen fertility higher than that observed in the interspecific F1 hybrid plant that served as a parent can comprise:

(1) preparing one or more BC1S2 plants by backcrossing an interspecific F1 hybrid pepper plant with its *C. annuum* parent, or with another *C. annuum* plant, to form a BC1 plant, selfing the BC1 plant to form one or more BC1S1 plants, and selfing the BCS1 plants to form one or more BC1S2 plants; and (2) selecting one or more BC1S2 plants with pollen that is more fertile than that of the interspecific F1 hybrid.

In addition to including and providing for methods of preparing progeny with a pollen fertility that is higher than that observed in the interspecific F1 hybrid plants, the present invention includes and provides for plants having higher pollen fertility than the F1 hybrid prepared by backcrossing of the interspecific F1 hybrid and selecting plants with higher pollen fertility as necessary. The present invention includes and provides for plants having higher pollen fertility than the F1 hybrid prepared by selfing (e.g. self pollination) of the interspecific F1 hybrid and selecting plants with higher pollen fertility as necessary. To avoid repetitions, reference is made with respect to pollen fertility to the full extent to the corresponding details provided above which apply equally to pollen fertility described here. More specifically, the present invention includes and provides for plants and plant populations of the F1 hybrid that have been backcrossed to the *C. annuum* parent of the interspecific hybrid as a recurrent parent, or with another *C. annuum* plant, and selected for pollen fertility to form subsequent generations of plants (e.g., BC1, BC2, BC3 . . . plants with higher pollen fertility), and seeds for such plants. The invention also includes and provides for plants and populations of plants that arise from selfing one or more plants produced from backcrosses of the interspecific F1 hybrid (e.g., BC1S1, BC1S2, or BC2S1) and seeds for such plants.

(2) Preparation of Crosses Between the Progeny of Interspecific F1 Hybrid Pepper Plants and *C. pubescens* (Preparation of Plants of a Second Cross)

In an aspect of the present invention, further improvements to the pollen fertility and the suitability of the plants of a first cross for the introgression of *C. pubescens* traits into *C. annuum* can be achieved by crossing a plant of a first cross with a *C. pubescens* plant or a *C. pubescens* hybrid to produce plants of a second cross (see Scheme 1 as depicted in FIG. 1). Plants of a second cross can also have improved ability to be crossed with other *Capsicum* plants (e.g., *C. annuum* plants and hybrids).

Methods of preparing plants of a second cross according to the present invention can include the steps of:
(1) preparing one or more plants of a first cross;
(2) selecting one or more plants of a first cross with pollen that is more fertile than that of the interspecific F1 hybrid to produce one or more selected plants of a first cross; and
(3) crossing the one or more selected plants of a first cross from (2) with a *C. pubescens* plant or a *C. pubescens* hybrid to produce one or more plants of a second cross or seeds therefrom.

In one aspect, plants of a second cross from (3) may be selected for pollen that is more fertile than that of the interspecific F1 hybrid to produce one or more selected plants of a second cross.

Pollen fertility of plants of a second cross can be assessed by determining the number of rounded pollen grains that stain well with a chromosome stain such as acetocarmine. Alternatively, pollen can be tested for their ability to pollinate *C. annuum* plants.

In one aspect of the present invention, plants of a second cross or seeds therefrom can be produced by
(1) preparing one or more plants of a first cross selected from BC1, BC2, BC3 BC2S1, BC1S1, BC1S2, F2, F3, F4, ann.×F1, ann./(ann.×F1), ann./ ann./(ann.×F1), ann.×F2, ann./(ann.×F2), ann.// ann./(ann.×F2), or ann.× F3 plants produced from an interspecific F1 hybrid pepper plant;
(2) selecting one or more plants of a first cross from (1) with pollen that is more fertile than that of the interspecific F1 hybrid used to prepare the plants of a first cross; and
(3) crossing the one or more of the selected plants from (2) with a *C. pubescens* plant to produce one or more plants of a second cross or seeds therefrom.

The methods may further comprise: (4) selecting one or more plants of a second cross from (3) for pollen that is more fertile than that of the interspecific F1 hybrid to produce one or more selected plants of a second cross.

In another aspect of the present invention, plants of a second cross can be produced by backcrossing interspecific F1 hybrids of *C. annuum* and *C. pubescens* at least once with the *C. annuum* parent of the interspecific F1 hybrid to form a plant of a first cross (e.g., a BC1, BC2, BC3, BC1S1, BC1S2, or BC2S1 plant), or with another *C. annuum* plant, which is subsequently crossed with a *C. pubescens* plant or a *C. pubescens* hybrid to form one or more plants of a second cross. The resulting plants of a second cross can be selected to have pollen that is more fertile than that of the interspecific F1 hybrid from which they were prepared to produce one or more selected plants of a second cross. Thus, in addition to the steps of forming an interspecific F1 hybrid pepper plant resulting from a cross between a *C. annuum* and a *C. pubescens*, methods of preparing one or more plants of a second cross, or seeds therefrom, can, for example, comprise:
(1) preparing one or more BC1, BC2, BC2S1, BC1S1 or BC1S2 plants by:
i) preparing BC1 plants by backcrossing the interspecific F1 hybrid pepper plant with its *C. annuum* parent, or with another *C. annuum* plant, to form the BC1 plant;
ii) preparing one or more BC2 progeny by backcrossing the interspecific F1 hybrid pepper plant with its *C. annuum* parent, or with another *C. annuum* plant, to form a BC1 plant, and backcrossing the BC1 plant with the *C. annuum* parent, or with another *C. annuum* plant, to form one or more BC2 plants;
iii) preparing one or more BC2S1 progeny by backcrossing the interspecific F1 hybrid pepper plant with its *C. annuum* parent, or with another *C. annuum* plant, to form a BC1 plant, backcrossing the BC1 plant with the *C. annuum* parent, or with another *C. annuum* plant, to form a BC2 plant, and selfing the BC2 plant to form one or more BC2S1 plants;
iv) preparing one or more BC1S1 plants by backcrossing an interspecific F1 hybrid pepper plant with its *C. annuum* parent, or with another *C. annuum* plant, to form a BC1 progeny and selfing the BC1 progeny to form one or more BC1S1 plants; or
v) preparing one or more BC1S2 plants by backcrossing an interspecific F1 hybrid pepper plant with its *C. annuum* parent, or with another *C. annuum* plant, to form a BC1 plant, selfing the BC1 plant to form a BC1S1 plants, and selfing the BCS1 plants to form one or more BC1S2 plants;
(2) selecting one or more BC1, BC2, BC2S1, BC1S1 or BC1S2 plants with pollen that is more fertile than that of the interspecific F1 hybrid to produce one or more selected BC1, BC2, BC2S1, BC1S1 or BC1S2 plants; and
(3) crossing the one or more selected BC1, BC2, BC2S1, BC1S1 or BC1S2 plants from (2) with a *C. pubescens* plant to produce one or more plants of a second cross or seeds therefrom.

The methods may further comprise: (4) selecting one or more plants of a second cross from (3) for pollen that is more fertile than that of the interspecific F1 hybrid to produce one or more selected plants of a second cross.

Other aspects of the present invention are drawn to plants of a second cross prepared from a specific cross. In one aspect, a method of preparing plants of a second cross is conducted by preparing one or more BC1 progeny, selecting one or more BC1 plants with pollen that is more fertile than that of the interspecific F1 hybrid, and crossing the selected BC1 plants with *C. pubescens* to produce one or more plants of a second cross. In another aspect, a method of preparing plants of a second cross is conducted by preparing one or more BC2 progeny, selecting one or more BC2 plants with pollen that is more fertile than that of the interspecific F1 hybrid, and crossing the selected BC2 plants with *C. pubes-*

*cens* to produce one or more plants of a second cross. In still another aspect, a method of preparing plants of a second cross is conducted by preparing one or more BC1S1 progeny, selecting one or more BC1S1 plants with pollen that is more fertile than that of the interspecific F1 hybrid, and crossing the selected BC1S1 plants with *C. pubescens* to produce one or more plants of a second cross. In other aspects, plants of second cross may be prepared by preparing BC2S1 or BC1S2 progeny of the interspecific F1 hybrid, crossing the progeny with a *C. pubescens* plant or *C. pubescens* hybrid to produce plants of a second cross, and selecting the plants for pollen fertility that is higher than that of the interspecific F1 hybrid. In each instance, these methods may further comprise: selecting one or more plants of a second cross for pollen that is more fertile than that of the interspecific F1 hybrid to produce one or more selected plants of a second cross.

In addition to methods of preparing plants of a second cross, a method of the present invention includes and provides for a plant of a second cross, seeds therefrom, and parts of a plant of a second cross including, but not limited to, plant seeds, pepper fruit, and cells.

(3) Preparation of Plants of a Third Cross

Where it is desired to prepare interspecific *C. annuum* hybrid plants, or seeds therefrom, having one or more traits introgressed from *C. pubescens*, plants of a second cross may be employed to prepare plants of a third cross or plants of a subsequent cross. Plants of a third cross may be prepared by crossing a plant of a second cross with a *C. annuum* plant or *C. annuum* hybrid (see Scheme 1 as depicted in FIG. 1).

In addition to the steps of preparing interspecific F1 hybrid pepper plants, methods of preparing one or more plants of a third cross or one or more seeds therefrom can comprise:

(1) preparing one or more plants of a first cross:
(2) selecting one or more plants of the first cross with pollen that is more fertile than that of the interspecific F1 hybrid that was used to produce the one or more plants of a first cross, to produce one or more selected plants of a first cross;
(3) crossing the one or more selected plants of a first cross from (2) with a *C. pubescens* plant or *C. pubescens* hybrid to produce one or more plants of a second cross; and
(4) crossing one or more plants of a second cross with a *C. annuum* plant or *C. annuum* hybrid produce one or more plants of a third cross or one or more seeds therefrom.

In one aspect, the one or more plants of a first cross are selected from BC1, BC2, BC3, BC2S1, BC1S1, BC1S2, F2, F3, F4, ann.×F1, ann./(ann.×F1), ann.//ann./(ann.×F1), ann.×F2, ann./(ann.×F2), ann.//ann./(ann.×F2), or ann.×F3 plants produced from an interspecific F1 hybrid pepper plant.

One aspect of the invention is directed to the preparation of plants of a third cross, seeds therefrom, and parts thereof using plants of a first cross prepared by backcrossing an interspecific F1 hybrid of *C. annuum* and *C. pubescens* with the *C. annuum* parent of the interspecific F1 hybrid, or with another *C. annuum* plant. In addition to the steps of preparing interspecific F1 hybrid pepper plants, methods of preparing one or more plants of a third cross, or one or more seeds therefrom can comprise:

(1) preparing one or more plants of a first cross by backcrossing an interspecific F1 hybrid pepper plant to the *C. annuum* parent of the interspecific F1 hybrid pepper plant, or with another *C. annuum* plant, at least once;
(2) selecting one or more plants of a first cross with pollen that is more fertile than that of the interspecific F1 hybrid to produce one or more selected plants of a first cross;
(3) crossing the one or more selected plants of a first cross from (2) with a *C. pubescens* plant to produce one or more plants of a second cross or seeds therefrom; and
(4) crossing one or more plants of a second cross with a *C. annuum* plant or *C. annuum* hybrid to produce one or more plants of a third cross or one or more seeds therefrom.

In one aspect, the plants of a first cross prepared in (1) by backcrossing an interspecific F1 hybrid pepper plant to the *C. annuum* parent of the interspecific F1 hybrid pepper plant, or with another *C. annuum* plant, at least once are selected from one or more of BC1, BC2, BC3, BC2S1, BC1S1, or BC1S2 plants produced from an interspecific F1 hybrid pepper plant.

In another aspect, the plants of a first cross prepared in (1) by backcrossing an interspecific F1 hybrid pepper plant to the *C. annuum* parent of the interspecific F1 hybrid pepper plant, or with another *C. annuum* plant, at least once are selected from one or more of BC1, BC2, BC1S1 plants produced from an interspecific F1 hybrid pepper plant.

In other aspects, of the present invention, the plants of a first cross prepared in (1) are selected from F2, F3, F4, ann.× F1, ann./(ann.×F1), ann.// ann./(ann.×F1), ann.×F2, ann./(ann.×F2), ann.// ann./(ann.×F2), or ann.×F3 plants produced from an interspecific F1 hybrid pepper plant.

(4) Preparation of Plants of a Subsequent Cross

In each aspect where plants of a third cross are prepared, the plants of a third cross may be crossed one or more times with a *C. annuum* plant, *C. annuum* hybrid or member of the *Capsicum* genus that is not *C. annuum* to prepare plants of a subsequent cross. Where plants of a third cross are prepared by more than one subsequent cross, a *C. annuum* plant, *C. annuum* hybrid or member of the *Capsicum* genus may be independently selected for each cross.

In some aspects a *C. annuum* plant will be used in the crosses with a plant of a third cross to prepare plants of a subsequent cross. In other aspects, a *C. annuum* hybrid will be used in the crosses with a plant of a third cross to prepare additional plants of a third cross. In still other aspects, where more than one additional cross is used to prepare plants of a subsequent cross, a *C. annuum* plant and a *C. annuum* hybrid will each be used in at least one cross with a plant of a third cross or its progeny to prepare plants of a subsequent cross.

For the preparation of plants of a subsequent cross s, a plant of a third cross can be backcrossed to the *C. annuum* plant or *C. annuum* hybrid used in its preparation from a plant of a second cross in one aspect. The crosses may be conducted one or more times, such that the *C. annuum* plant or *C. annuum* hybrid is a recurrent parent to used to produce a desired progeny plant or seeds therefrom. In another aspect, plants of a third cross can be crossed with a *C. annuum* plant or *C. annuum* hybrid that is not a recurrent parent.

In one aspect, at least two additional crosses of a plant of a third cross are used to form plants of a subsequent cross. In another aspect, at least three additional crosses are used to form plants of a subsequent cross.

To prepare plants of a subsequent cross, plants of a third cross can be subject to one or more steps of selfing, or one or more crosses with a *C. annuum* plant, a *C. annuum* hybrid, or a member of the *Capsicum* genus that is not *C. annuum*, that has been independently selected for each cross or any combination of crosses, to produce plants of a subsequent cross, or seeds therefrom. In addition, plants of a third cross may be selfed one or more times, or crossed one or more times with *C. annuum* plant, *C. annuum* hybrid, or other members of the *Capsicum* genus, or hybrids thereof, including, but not limited to *C. baccatum, C. cardenasii, C. chacoense, C. chinense, C. ciliatum, C. eximium, C. flexuosum, C. frutescens, C. gal-*

*apagoense, C. praetermissum, C. pubescens,* or *C. tovarii,* that have been independently selected for each cross or combination of crosses to produce hybrid plants and seeds therefrom. In one aspect, plants of a third cross, including plants of a subsequent cross, may be selfed one or more times, or crossed one or more times with a *C. annuum* plant, *C. annuum* hybrid, or other members of the *Capsicum* genus, or hybrids thereof, including *C. cardenasii, C chinense, C. eximium, C. frutescens, C. praetermissum,* or *C. pubescens,* that have been independently selected for each cross or combination of crosses to produce hybrid plants and seeds therefrom.

One aspect of the present invention is directed to plants of a third cross, including plants of a subsequent cross, that have been prepared using only white flowered *Capsicum* species *C. annuum, C. baccatum, C. chacoense, C. chinense, C. frutescens, C. galapagoense, C. praetermissum,* and the purple flowered species *C. pubescens.* Such a plant may be selfed one or more times, or crossed one or more times with *C. annuum* plants, *C. annuum* hybrids, or other members of the *Capsicum* genus, or hybrids thereof, including, *C. annuum, C. baccatum, C. chacoense, C. chinense, C. frutescens, C. galapagoense, C. praetermissum and C. pubescens,* that have been independently selected for each cross or combination of crosses to produce hybrid plants and seeds therefrom. Such a plant may have no nuclear genetic material derived *C. eximium, C. tovarii* or *C. cardenasii.* Alternatively, such plants, which can be fertile (non-sterile), may have no nuclear DNA specific or unique to one or more plants selected from *C. cardenasii, C. eximium,* and *C. tovarii.*

*C. annuum* plants or *C. annuum* hybrids that can be employed in any cross with plants of a first cross, second cross, or third cross, or with plants of a subsequent cross, include, but are not limited to, pepper plants that produce sweet pepper fruit, mild pepper fruit, medium pepper fruit, hot pepper fruit, and very hot pepper fruit, where the pepper fruit has a shape selected from the group consisting of block, pointed and round, and where the pepper fruit has a color selected from the group consisting of green, red, yellow, orange, purple, brown and white. *C. annuum* plants or hybrids that can be employed in any cross with an interspecific F1 hybrid plant of a first cross, plant of a second cross, or plant of a third cross also include, but are not limited to, a pepper plant of a named variety.

(5) Selection of Plants of First, Second, or Third Crosses, or Plants of a Subsequent Cross with Desired Phenotypic Traits A progeny of an interspecific F1 hybrid that results from crossing a *C. annuum* plant or hybrid and a *C. pubescens* plant or hybrid can be prepared by a variety of different crosses between the interspecific F1 hybrid and other plants of the *Capsicum* genus. A progeny, including plants of a first cross, plants of a second cross, or plants of a third cross (including plants of a subsequent cross) can be screened or selected for a variety of traits or nuclear genetic material, introgressed from *C. pubescens* plants or *C. pubescens* hybrids, to produce selected plants and seeds therefrom having the desired trait.

As *C. annuum* plants or *C. annuum* hybrids that can be employed in any cross with an interspecific F1 hybrid, plant of a first cross, plant of a second cross, or plant of a third cross (including plants of a subsequent cross) can have a variety of traits, those traits can be bred into their progeny. To avoid repetition, reference is made with respect to the traits of pepper plants (a) through (mm) to the full extent to the corresponding details provided above which apply equally to the specified traits. *C. annuum* plants or *C. annuum* hybrids that can be employed in crosses include, but are not limited to, plants that produce sweet pepper fruit, mild pepper fruit, medium pepper fruit, hot pepper fruit, and very hot pepper fruit, where the pepper fruit has a shape selected from the group consisting of block, pointed and round, and where the pepper fruit has a color selected from the group consisting of green, red, yellow, orange, purple, brown and white. *C. annuum* plants or hybrids that can be employed in any crosses also include, but are not limited to pepper plants of a named variety, whose traits, including taste and other traits can be bred into and selected for in their progeny, particularly where they are employed as a recurrent parent.

In one aspect of the present invention, the plants to be screened or selected will be the progeny of an interspecific F1 hybrid pepper plant resulting from the cross of a *C. annuum* plant or hybrid and a *C. pubescens* plant or hybrid. Those progeny include, but are not limited to, BC1, BC2, BC3, BC4, BC1S1, BC1S2, BC2S1, BC2S2, F2, F3, F4, ann.×F1, ann./(ann.×F1), ann.// ann./(ann.×F1), ann.×F2, ann./(ann.×F2), ann.// ann./(ann.×F2), ann.×F3, ann./(ann.×F3), or ann.//ann./(ann.×F3) plants. Methods of preparing one or more of such plants may further comprise a step of selecting one or more of the plants either for one or more traits introgressed from *C. pubescens* such as resistance, tolerance and immunity to geminiviruses, tobamoviruses, and *Xanthomonas*, (which indicates the presence of *C. pubescens* nuclear genetic material) or for nuclear genetic material from *C. pubescens.*

In other aspects, plants to be screened or selected will be plants of a first cross or plants of a second cross. The methods of preparing plants of a first cross or plants of a second cross may further comprise a step of selecting one or more of the plants either for one or more traits introgressed from *C. pubescens* or for nuclear genetic material from *C. pubescens* as above.

In another aspect, methods of preparing and screening plants of a third cross comprise preparing one or more plants of a first cross, selecting one or more plants of a first cross with pollen that is more fertile than that of the interspecific F1 hybrid that served as the predecessor of the plants of the first cross, crossing the selected plants of the first cross with a *C. pubescens* plant or *C. pubescens* hybrid to produce one or more plants of the second cross, crossing the one or more plants of a second cross with a *C. annuum* plant or a *C. annuum* hybrid one or more times to produce one or more plants of a third cross or a seed therefrom, and selecting the plant of a third cross either for one or more traits introgressed from *C. pubescens* or for nuclear genetic material from *C. pubescens* as above. In one aspect, one or more plants of a first cross are BC1 plants prepared from the interspecific F1 hybrid that served as their predecessor. In other aspects, plants of a first cross are BC1, BC2, BC1S1, BC2S1, or BC1S2 plants prepared from a interspecific F1 hybrid that served as their predecessor. In still other aspects, plants of a first cross are F2, F3, or F4 progeny of an interspecific F1 hybrid that served as their predecessor. In still other aspects, plants of a first cross are ann.×F1, ann./(ann.×F1), ann.// ann./(ann.×F1), ann.×F2, ann./(ann.×F2), ann.// ann./(ann.× F2), or ann.×F3 plants prepared from the interspecific F1 hybrid that served as their predecessor.

In another aspect, where the plants to be screened or selected are plants of a third cross, the method of preparing plants of a third cross can further comprise a step of selecting one or more of the plants either for one or more traits introgressed from *C. pubescens* or for nuclear genetic material from *C. pubescens.* In one particular aspect methods of preparing plants of a third cross further comprise:

(1) preparing one or more plants of a first cross by backcrossing an interspecific F1 hybrid pepper plant to the *C.*

*annuum* parent of the interspecific F1 hybrid pepper plant at least once or a *C. annuum* plant at least once;

(2) selecting one or more plants of a first cross with pollen that is more fertile than that of the interspecific F1 hybrid to produce one or more selected plants of a first cross;

(3) crossing the one or more selected plants of a first cross from (2) with a *C. pubescens* plant to produce one or more plants of a second cross, or seeds therefrom; and (4) crossing one or more plants of a second cross with a *C. annuum* plant or *C. annuum* hybrid to produce one or more plants of a third cross, or one or more seeds therefrom.

(5) selecting one or more plants of a third cross from (4) either for one or more phenotypic traits introgressed from *C. pubescens* (which indicates the presence of *C. pubescens* nuclear genetic material), or for nuclear genetic material from *C. pubescens*.

(6) Phenotypic Traits

The traits of pepper plants produced by methods described herein include the traits for pungency (trait r as provided above), fruit shape (trait s-bb as provided above), and fruit color (trait p, q, ff, and gg as provided above). In some aspects, plants with those traits are selected from plants that produce sweet pepper fruit, mild pepper fruit, medium pepper fruit, hot pepper fruit, and very hot pepper fruit, where the pepper fruit has a shape selected from the group consisting of block, pointed and round, and where the pepper fruit has a color selected from the group consisting of green, red, yellow, orange, purple, brown and white.

Pepper plants produced by methods described herein may also have the traits of a named variety, particularly where the named variety is used as a recurrent parent, such crosses will result in the production of plants, and seeds therefrom, where the plants have one or more traits from *C. pubescens* introgressed into the background of the *C. annuum* variety that served as the recurrent parent, provided the traits are selected for during the crosses with the recurrent parent.

In addition to pungency, fruit shape, and fruit color, a variety of phenotypic traits from *C. pubescens* can be bred into the progeny of F1 interspecific hybrid pepper plants resulting from a cross between *C. annuum* and *C. pubescens*, including plants of a first, second, or third cross, or into plants of a subsequent cross. The progeny may be subsequently selected for plants with one or more traits, and for the production of seeds that produce a plant having the trait(s).

Among the traits that can be selected are geminivirus resistance, tobamovirus resistance, *Xanthomonas* resistance, ease of fruit shedding, cold tolerance, leaf hair, flower coloration (e.g., purple flower, purple style, purple anther filament), black seeds, fruit color, thick fruit walls, flavor differences, and the clustering of seed-bearing placental tissue close to the stem of the fruit. In one aspect, the phenotypic trait that is selected for is selected from leaf hair, purple flower, purple style, purple anther filament, fruit color, and seed color (black seed).

One aspect of the present invention is the introduction of resistance to diseases and pests that affect members of the *Capsicum* genus, particularly *C. annuum*, into plants of a first, second, or third cross, or into plants of a subsequent cross. In one aspect, a trait is resistance to a geminivirus. In another aspect, a trait is resistance to a tobamovirus. In another aspect a trait is *Xanthomonas* resistance. In other aspects, a trait is resistance to aphids, particularly resistance to green peach aphid (*Myzus persicae* (Sulzer)), or resistance to powdery mildew (*Leveillula taurica*).

In one aspect, the present invention is directed to and includes plants having a resistance to a disease or pest. Resistance of any of the pepper plants provided herein can be measured by any means available in the art. Resistance of any pepper plant provided herein can be complete resistance or partial resistance. In one aspect, resistance is determined relative to a non-resistant or susceptible plant. In another aspect, resistance is determined relative to a non-resistant or susceptible parent plant. Resistance may be identified by a delay in symptoms compared to a non-resistant or susceptible plant. In another aspect, plants having a resistance to a disease or pest may be identified by a reduced severity of symptoms compared to a non-resistant plant. In yet another aspect, plants having a resistance to a disease or pest may be identified by a delay in symptoms and a reduced severity compared to a non-resistant plant. In yet another aspect, resistance may be identified indirectly. In one aspect, resistance may be observed as higher yield in the resistant plant relative to a non-resistant or susceptible plant after exposure to the disease or pest. In another aspect, resistance may be observed as more vigourous growth in the resistant plant relative to a non-resistant or susceptible plant after exposure to the disease or pest. In one aspect, resistance may be quantified on a resistance scale.

In one aspect of the present invention, tobamovirus resistance may be read on a Resistant (R) or Hypersensitive (HR) versus Susceptible (S) scale. Hypersensitive response is a well known phenomenon where a localized cell death is observed in resistant plants. See Mur et. al., The hypersensitive response; the centenary is upon us but how much do we know?, 59 *J. Exp. Botany* 501-520 (2008). Plants showing a HR response are known sources of resistance traits. Plants that have no dark spots present on the leaves or stem or only have a light mottling throughout the plant on the leaves are given a resistant rating of 1 (HR or R). Plants that have dark spots on the leaves and or stem are assigned a susceptible rating of 9 (S). Symptoms may also include leaf distortion, leaf curling, severe stunting, reduced leaf size, and in severe cases, reduction in flower and fruit production, such as number and size of flower, fruit or flower and fruit. Further symptoms may be chlorosis, mottling, reduced leaf size, darkened veins, vein swelling, enations, and flower and fruit drop. In another aspect, geminivirus may be assayed using the same resistance scale.

In other aspects, of the present invention, a trait introgressed into *C. annuum* from *C. pubescens* is a fruit trait selected from ease of fruit shedding, black seeds, fruit color (e.g., green, yellow, orange red, purple, brown, and white), and the clustering of seed-bearing placental tissue close to the stem of the fruit. In other aspects, a selected fruit trait is ease of fruit shedding, black seeds, or fruit color (e.g., green, yellow, orange, and red). In still another aspect, a fruit trait is the clustering of seed-bearing placental tissue close to the stem of the fruit.

As *C. annuum* hybrids may be employed in the preparation of plants of a first, second, or third cross, or plants of a subsequent cross, one or more traits found in *C. annuum* hybrids may be used as an additional source of traits to be incorporated into, and selected for in those plants. Such one or more traits include resistance to disease (bacterial, fungal, or viral) and pests (e.g. insects). *C. annuum* hybrids may also have one or more traits that can be bred into plants of a first, second, or third cross, or plants of a subsequent cross. In one aspect, the one or more of those traits that are independently selected for consist of: growth habits, stem morphology (e.g., glabrous or pubescent), leaf morphology (e.g., glabrous or pubescent), stem color, pedicle position at anthesis, corolla color, anther color, filament color, stigma position relative to the anthers at full anthesis, male sterility or fertility, fruit set, seed color, calyx margin shape, shape at the junction of the calyx and peduncle, fruit position, immature fruit color, mature fruit color, fruit pungency (e.g., sweet or hot), fruit length at ripeness, fruit wall thickness, fruit width at ripeness, persistence of fruit, fruit weight, fruit shape, fruit shape at the point of stem attachment, fruit shape at the blossom end, cross section shape, resistance to insects, resistance to bacterial disease, resistance to viral disease, resistance to fungal disease, the presence of anthocyanins in unripe or ripe pepper fruit, temperature susceptibility to high or low temperature, susceptibility to drought or high humidity, susceptibility to high soil moisture, and ease of fruit shed.

Other traits that can be selected for are plant morphological traits including but not limited to determinate growth (having terminal flower nodes), indeterminate growth (lacking terminal flower nodes). To avoid repetition, reference is made with respect to the traits of pepper plants (a) through (mm) to the full extent to the corresponding details provided above which apply equally to plant morphological traits.

In one aspect, the *C. annuum* hybrids employed as a source of traits to be introgressed into plants of a first, second, or third cross, or plants of a subsequent cross, may be *C. annuum* hybrids having introgressions from one or more *Capsicum* species selected from the group consisting of *C. baccatum*, *C. chacoense*, *C. chinense*, *C. frutescens*, *C. galapagoense*, and *C. praetermissum*. In another aspect the *C. annuum* hybrids may be hybrids having introgressions from one or more *Capsicum* species selected from the group consisting of *C. baccatum*, *C. chacoense*, *C. chinense*, and *C. frutescens*.

Plants of first, second, or third crosses, or plants of a subsequent cross, can also be selected for nuclear genetic material from *C. annuum* or *C. pubescens*. The presence of nuclear genetic material (nucleic acids) from *C. pubescens* in interspecific hybrids of *C. annuum* can be detected by any method known in the art, including, but not limited to, the detection of restriction fragment length polymorphisms, the detection of markers by PCR or hybridization techniques (e.g., Northern or Southern blots) or sequence analysis.

In one aspect of the invention, where the trait is resistance to *Xanthomonas*, plants of the invention may be selected for the presence of the Bs4 gene (e.g., the Bs4 gene of *C. pubescens* P1235047). In one aspect, plants of a first, second, or third cross, or plants of a subsequent cross, that are resistant to *Xanthomonas* sp., particularly *Xanthomonas campestris* pv. vesicatoria, are not the progeny of *C. tovarii*, *C. cardenasii*, or *C. eximium*, and do not have nuclear genetic material derived from those *Capsicum* species.

(7) Plants, Plant Parts, Including Seeds

The present invention includes and provides for plants, and seeds therefrom, which seeds when grown produce one or more plants with traits from the plants of its parentage that have been selected for. The present invention also includes parts of such plants including the pepper fruit, and cells or protoplasts of such plants, particularly where the cells or protoplasts are present in a tissue culture of cells or protoplasts.

Pepper plants produced by methods of the present invention may be pepper plants that produce sweet pepper fruit, mild pepper fruit, medium pepper fruit, hot pepper fruit, or very hot pepper fruit, where the pepper fruit has a shape selected from the group consisting of block, pointed and round, and where the pepper fruit has a color selected from the group consisting of green, red, yellow, orange, purple, brown and white. Such plants include pepper plants of a first cross, second cross, or third cross, or plants of a subsequent cross, parts thereof, including seeds therefrom.

Plants of a first cross, second cross, or third cross, or plants of a subsequent cross, include plants of a named variety (named *C. annuum* variety) having one or more traits introgressed from *C. pubescens*. Such plants are prepared with a pepper plant of a named variety employed as a recurrent parent, which result in the production of plants, and seeds therefrom, where the plants having one or more traits from *C. pubescens* introgressed into the background of the *C. annuum* variety that served as the recurrent parent, provided the traits are selected for during the crosses with the recurrent parent.

The present invention includes and provides for plants of a first cross, second cross, or third cross, or plants of a subsequent cross, parts thereof, and seeds therefrom, having one or more traits selected from the group consisting of geminivirus resistance, tobamovirus resistance, *Xanthomonas* resistance, ease of fruit shedding, cold tolerance, leaf hair, flower coloration (purple flower, purple style, purple anther filament), black seed color, fruit color, thick fruit walls, flavor differences, and the clustering of seed-bearing placental tissue close to the stem of the fruit into *C. annuum* plants.

The present invention includes and provides for plants of a first cross, second cross, or third cross, or plants of a subsequent cross, parts thereof, and seeds therefrom, having one or more disease or pest resistances. In one aspect, the plants have resistance to one or more viral diseases, bacterial diseases, fungal diseases or pests that affect members of the *Capsicum* genus, particularly *C. annuum*, where at least one resistance is derived from a *C. pubescens* parent. In one aspect, a trait is resistance to a geminivirus. In another aspect a trait is resistance to a tobamovirus. In another aspect a trait is *Xanthomonas* resistance. In other aspects, a trait is resistance to aphids, particularly resistance to green peach aphid (*Myzus persicae* (Sulzer)), or resistance to powdery mildew (*Leveillula taurica*).

Included in the present invention are plants of a first cross, second cross, or third cross, or plants of a subsequent cross, parts thereof, and seeds therefrom, having one or more traits independently selected the traits consisting of: growth habits, stem morphology (e.g., glabrous or pubescent), leaf morphology (e.g., glabrous or pubescent), stem color, pedicle position at anthesis, corolla color, anther color, filament color, stigma position relative to the anthers at full anthesis, male sterility or fertility, fruit set, seed color, calyx margin shape, shape at the junction of the calyx and peduncle, fruit position, immature fruit color, mature fruit color, fruit pungency (e.g., sweet or hot), fruit length at ripeness, fruit wall thickness, fruit width at ripeness, persistence of fruit, fruit weight, fruit shape, fruit shape at the point of stem attachment, fruit shape at the blossom end, cross section shape, resistance to insects, resistance to bacterial disease, resistance to viral disease, resistance to fungal disease, the presence of anthocyanins in unripe or ripe pepper fruit, temperature susceptibility to high or low temperature, susceptibility to drought or high humidity, susceptibility to high soil moisture, and ease of fruit shed.

Plants of a first cross, second cross, or third cross, or plants of a subsequent cross may be determinate growth (having terminal flower nodes), or indeterminate growth (lacking terminal flower nodes) plants.

One aspect of the present invention is directed to and includes plants of a first, second, or third cross, or plants of a subsequent cross, having introgressions from one or more *Capsicum* species selected from the group consisting of *C. baccatum*, *C. chacoense*, *C. chinense*, *C. frutescens*, *C. galapagoense*, and *C. praetermissum*. Another, aspect of the present invention is directed to and includes plants of a first, second, or third cross, or plants of a subsequent cross, having introgressions from one or more *Capsicum* species selected from the group consisting of *C. baccatum, C. chacoense, C. chinense*, and *C. frutescens*. Yet another, aspect of the present invention is directed to and includes plants of a first, second, or third cross, or plants of a subsequent cross, having introgressions from one or more *Capsicum* species selected from the group consisting of *C. baccatum, C. chinense*, and *C. frutescens*.

In one aspect, the present invention includes and provides for plants of a first, second, or third cross, or plants of a subsequent cross, where the plants do not have one or more plants of a *Capsicum* species selected from *C. cardenasii, C. eximium*, and *C. tovarii* as an ancestor. Such plants, which can be fertile, have no nuclear DNA specific or unique to one or more plants selected from *C. cardenasii, C. eximium*, and *C. tovarii*. The plants may be prepared by using ancestral plants that are not *C. cardenasii, C. eximium*, or *C. tovarii* or the progeny of *C. cardenasii, C. eximium*, and *C. tovarii* (i.e., neither *C. annuum* hybrids nor *C. pubescens* hybrids have *C. cardenasii, C. eximium*, and *C. tovarii* as an ancestor). In one aspect, plants that do not have *C. cardenasii, C. eximium*, and *C. tovarii* as an ancestor can be distinguished by phenotype including growth habits, stem morphology (e.g., glabrous or pubescent), leaf morphology (e.g., glabrous or pubescent), stem color, pedicle position at anthesis, corolla color, anther color, filament color, stigma position relative to the anthers at full anthesis, male sterility or fertility, fruit set, seed color, calyx margin shape, shape at the junction of the calyx and peduncle, fruit position, immature fruit color, mature fruit color, fruit pungency (e.g., sweet or hot), fruit length at ripeness, fruit wall thickness, fruit width at ripeness, persistence of fruit, fruit weight, fruit shape, fruit shape at the point of stem attachment, fruit shape at the blossom end, cross section shape, resistance to insects, resistance to bacterial disease, resistance to viral disease, resistance to fungal disease, the presence of anthocyanins in unripe or ripe pepper fruit, temperature susceptibility to high or low temperature, susceptibility to drought or high humidity, susceptibility to high soil moisture, and ease of fruit shed.

In another aspect, plants that have no nuclear DNA specific or unique to one or more plants selected from *C. cardenasii, C. eximium*, and *C. tovarii* can be identified by methods known to one of skill in the art including reassociation rate methods (e.g. $C_0t$ and $R_0t$ analysis), hybridization studies (e.g. dot, slot blots), genome sequencing and PCR. Plants are considered to have no nuclear DNA specific or unique to one or more plants selected from *C. cardenasii, C. eximium*, and *C. tovarii* when measured levels are within 3× the standard deviation of non-specific control background levels.

Also included in the scope of the present invention are parts of such plants, including their seeds and pepper fruit. Plants regenerated from embryos, cells, protoplasts, and tissue cultures of cells or protoplasts, having an F1 hybrid pepper plant produced by crossing *C. annuum* and *C. pubescens* as an ancestor are also within the scope of the present invention.

The present invention includes and provides for a pepper plant, which may be fertile, and parts thereof produced by any of the methods of the present invention, or a seed therefrom, which seed when grown produces a pepper plant of the present invention. In one aspect, seed for pepper plants produced by the methods of the present invention contain some nuclear genetic material or nucleic acid sequences derived from a *C. pubescens* plant. A plant of the present invention may comprise less than about 0.2%, 0.5%., 1%, 2%, 5%, 7.5%, 10%, 15%, 20%, or 25% of their nuclear DNA content derived from a *C. pubescens* plant.

In one aspect, where plants of a first, second, or third cross, or plants of a subsequent cross have less than about 0.2%, 0.5%, 1%, 2%, 5%, 7.5%, 10%, 15%, 20%, or 25% of its nuclear DNA content derived from a *C. pubescens* plant, a plant may have a restricted parentage. A plant of the present invention may comprise about 0.2% to 25%, 0.5% to 25%, 1.0% to 25%, 2.0% to 25%, 5% to 25%, 7.5% to 25%, 10% to 25%, 15% to 25% or 20-25% of their nuclear DNA content derived from a *C. pubescens* plant. In one aspect, where plants have restricted parentage a plant may not be the progeny of a *Capsicum* species selected from *C. cardenasii, C. eximium*, and *C. tovarii* (i.e. they lack nuclear DNA specific or unique to one or more of *C. cardenasii, C. eximium*, and *C. tovarii*). In other aspects, such plants may have one or more introgressions from a *Capsicum* species selected from *C. baccatum, C. chacoense, C. chinense, C. frutescens, C. galapagoense*, and *C. praetermissum*; or alternatively, the group may be selected from *C. baccatum, C. chacoense, C. chinense*, and *C. frutescens*. In another aspect, plants of a first, second, or third cross, or plants of a subsequent cross may not be the progeny of a *Capsicum* species selected from *C. cardenasii, C. eximium*, and *C. tovarii* and may have one or more introgressions from a *Capsicum* species selected from *C. baccatum, C. chacoense, C. chinense, C. frutescens, C. galapagoense* and *C. praetermissum*. Alternatively, a plant may not be the progeny of a *Capsicum* species selected from *C. cardenasii, C. eximium*, and *C. tovarii* and may have one or more introgressions from a *Capsicum* species selected from *C. baccatum, C. chacoense, C. chinense*, and *C. frutescens*.

In a further aspect of the present invention, plants of a third cross, or plants of a subsequent cross, have less than about 0.2%, 0.5%, 1%, 2%, 5%, 7.5%, 10%, 15%, 20%, or 25% of their nuclear DNA content derived from a *C. pubescens* plant, and greater than about 50%, 60%, 75%, 80%, 85%, 90%, 92.5%, 95%, 98%, 99%, 99.5% 99.8%, 99.9%, 99.95%, or 99.99% of its nuclear DNA derived from a *C. annuum* plant, and may have a restricted parentage. Thus, for example, a plant of a third cross may be a plant having: less than about 2% of its nuclear DNA derived from a *C. pubescens* plant; greater than about 90% of its nuclear DNA derived from a *C. annuum* plant; where the plant has no nuclear DNA specific or unique to one or more plants selected from *C. cardenasii, C. eximium*, and *C. tovarii*; and where the plant optionally contains one or more introgressions from a plant of a *Capsicum* species selected from the group consisting of *C. baccatum, C. chacoense, C. chinense*, and *C. frutescens*.

The percentage of nuclear DNA, or lack thereof, derived from *C. pubescens* or *C. annuum* can be determined by any technique known in the art including sequencing and analyzing genetic markers present in the genome of either *C. pubescens* or *C. annuum* or both *C. pubescens* or *C. annuum*. A number of markers and maps for *C. annuum* have been published including, but not limited to, those described in Ben Chaim A. et al., *QTL mapping of fruit related traits in pepper (Capsicum annuum)*. Theor. Appl. Genet. 102: 1016-1028 (2001) and Lefebvre V. et al., *Towards the saturation of the pepper linkage map by alignment of three intraspecific maps including known-function genes*, Genome 45(5): 839-54 (2002), hereby incorporated by reference in its entirety. Marker analysis may be conducted by methods including, but not limited to use of, nucleic acid hybridization, FISH (fluorescent in situ hybridization), PCR, and restriction fragment length polymorphism analysis.

The present invention includes and provides for a part of a plant selected from: an interspecific F1 hybrid prepared by crossing a *C. annuum* plant or *C. annuum* hybrid with a *C. pubescens* plant or *C. pubescens* hybrid; a plant of a first cross; second cross; third cross; or an additional plant of a third cross. A part of a plant includes, but is not limited to, a part selected from a: leaf, pollen, embryo, cotyledon, hypocotyl, meristematic cell, root, root tip, anther, flower, seed or stem. Such plants and plant parts my further comprise one or more transgenes. Transgenes may contribute to the phenotype of the plants and provide for traits such as herbicide resistance.

The present invention also includes and provides for a tissue culture of regenerable cells or protoplasts from: an interspecific F1 hybrid between a *C. annuum* plant or hybrid and a *C. pubescens* plant or hybrid; a plant of a first cross, second cross, third cross; or an additional plant of a third cross. A tissue culture of regenerable cells includes, without limitation, a tissue culture of cells or protoplasts from a tissue selected from leaves, pollen, embryos, roots, root tips, anthers, flowers, fruit, or seeds. Also included and provided for are plants derived from a tissue culture of the regenerable cells, particularly those plants that have the physiological and morphological traits of the plant used to produce the tissue culture.

(8) Bridge Crosses

In addition to methods that employ direct crosses to produce hybrids between *C. annuum* and *C. pubescens*, the present invention includes methods employing a bridging species to prepare hybrids between *C. annuum* and *C. pubescens* and seeds that when grown produce a plant that is a hybrid between *C. annuum* and *C. pubescens* including:

(a) performing a first cross between either a *C. annuum* plant or *C. annuum* hybrid and a plant of a bridging *Capsicum* species selected from the group consisting of: *C. chinense, C. baccatum, C. praetermissum*, and *C. eximium* to form a *C. annuum* hybrid, and crossing one or more progeny from the first cross with *C. pubescens* to form hybrid seeds that when grown produce plants that are a hybrid between *C. annuum* and *C. pubescens*.

The present invention also includes hybrids between *C. annuum* and *C. pubescens* and seeds that when grown produce a plant that is a hybrid between *C. annuum* and *C. pubescens* by performing a first cross between *C. pubescens* and *C. cardenasii*, and crossing one or more progeny from the first cross with a *C. annuum* plant or *C. annuum* hybrid to form a hybrid seed that when grown produces a plant which is a hybrid between *C. annuum* and *C. pubescens*.

In some aspects, a method of producing plants according to the present invention using a bridging species further comprises one or more additional steps of crossing a hybrid between *C. annuum* and *C. pubescens* with a *C. annuum* plant or hybrid. Alternatively, a method can further comprise two or more additional steps of crossing the hybrid of *C. annuum* and *C. pubescens* with a *C. annuum* plant or hybrid as a recurrent parent.

In some aspects, a method of producing plants using a bridging species further comprises selecting plants at one or more generations for one or more traits selected from the group consisting of: aphid resistance, powdery mildew resistance, geminivirus resistance, tobamovirus resistance, *Xanthomonas* resistance, ease of fruit shedding, cold tolerance, leaf hair, flower color (purple flower corolla, purple style, purple anther filament), leaf wrinkle, black seed color, fruit color, thick fruit walls, flavor differences, and the clustering of seed-bearing placental tissue close to the stem of the fruit into *C. annuum* plants.

The methods of using a bridging species to produce hybrids of *C. annuum* and *C. pubescens*, or a seed therefrom, include the production of pepper plants and their seeds, having one or more *C. pubescens* traits introgressed into specific varieties of *C. annuum* plants. In some aspects, the *C. annuum* variety is selected from a bell pepper, sweet pepper, green pepper, red pepper or hot pepper varieties. In other aspects, the *C. annuum* variety is a pepper plant of a named variety.

The present invention includes and provides for pepper plants, and parts thereof, including seeds therefrom, produced by any of the methods of producing pepper plants using a bridging species having one, two, three, four, five, six, seven or more traits from *C. pubescens* introgressed into a *C. annuum* background. In one aspect, the one, two, three, four, five, six, seven, or more traits are selected from the group consisting of: geminivirus resistance, tobamovirus resistance, *Xanthomonas* resistance, ease of fruit shedding, cold tolerance, leaf hair, purple flower, purple style, purple anther filament, leaf wrinkle, black seed color, fruit color, thick fruit walls, flavor differences, and the clustering of seed-bearing placental tissue close to the stem of the fruit. In particular, the invention includes a hybrid pepper plant having one or more traits from *C. pubescens* introgressed into a *C. annuum* background, where the traits introgressed from *C. pubescens* are selected from the group consisting of: geminivirus resistance, tobamovirus resistance, *Xanthomonas* resistance, ease of fruit shedding, cold tolerance, leaf hair, purple flower, purple style, purple anther filament, leaf wrinkle, black seed color, fruit color, thick fruit walls, flavor differences, and the clustering of seed-bearing placental tissue close to the stem of the fruit.

In one aspect, the present invention includes a hybrid pepper plant produced by using bridging species having one or more traits from *C. pubescens* introgressed into a *C. annuum* background, where the traits are selected from the group consisting of: geminivirus resistance, tobamovirus resistance, and *Xanthomonas* resistance. In another aspect, a hybrid plant produced by using a bridging species is a plant that produces sweet pepper fruit, mild pepper fruit, medium pepper fruit, hot pepper fruit, or very hot pepper fruit; where the pepper fruit have a shape selected from the group consisting of block, pointed and round, and where the pepper fruit has a color selected from the group consisting of green, red, yellow, orange, purple, brown and white. In yet other aspects, the pepper plants, or seeds therefrom, are a variety selected from the group consisting of: a pepper plant of a named variety.

The present invention also includes a part of a hybrid pepper plant produced using a bridging species, particularly those that have been selected for one or more of the above-mentioned traits.

The present invention includes a tissue culture of regenerable cells of a hybrid pepper plant produced using a bridging species, particularly those plants that have been selected for one or more of the above-mentioned traits.

(9) Aspects of a Hybrid Plant and a Method of its Preparation

Whether plants are plants of a first, second, third, plants of a subsequent cross, or plants produced by bridge crosses, it is possible to select for such plants with desired traits using a variety of schemes. In one aspect, plant selection is conducted en masse at one or more of the steps in their preparation. Alternatively, plants may be screened and selected in groups or individually for desired traits at one or more steps in their preparation.

In another aspect, selection either for one or more phenotypic traits introgressed from *C. pubescens*, or for nuclear genetic material from *C. pubescens*, may be conducted using selection en masse, or selection of individual plants or any combination thereof. It is also possible to employ any combination of en masse selection, group selection, and individual selection.

While plants of a first, second, third, plants of a subsequent cross, or plants produced by bridge crosses, may be prepared using a *C. annuum* plant or *C. annuum* hybrid as a *C. annuum* parent, and a *C. pubescens* plant or *C. pubescens* hybrid as *C. pubescens* parent, in some aspects one or more hybrids are not employed at one or more steps in their preparation. In one aspect, for example, plants are prepared using *C. annuum* plants or *C. annuum* hybrids and a *C. pubescens* plants, but not *C. pubescens* hybrids in the initial crosses to form F1 plants or in subsequent crosses.

Methods of the present invention makes possible the production of interspecific hybrids of *C. annuum* and *C. pubescens*. Such hybrids can consist of nucleic acid sequences derived from only those two species. In some aspects, where a bridging species is employed to accomplish the cross, nuclear genetic material from the bridging species can be bred out, for example by using a *C. annuum* plant as a recurrent parent while selecting for a *C. pubescens* trait. The nuclear genome of plants of the present invention or seeds therefrom, can have a nuclear genetic makeup that is principally that of a *C. annuum* plant. In one aspect, a plant of the present invention, or seeds therefrom, consist essentially of, or comprise nuclear genetic material from *C. annuum* and *C. pubescens* and any other genes that have been introduced from plants outside of the *Capsicum* genus (e.g., transgenes including those for herbicide resistance, pathogen resistance, insect pest resistance etc.). Plants of the present invention, or seeds therefrom, may comprise less than about, 0.2%, 0.5%, 1%, 2%, 5%, 7.5%, 10%, 15%, 20%, or 25% of their nuclear DNA content derived from a *C. pubescens* plant. Plant of the present invention, or seeds therefrom, may comprise greater than about 50%, 60%, 75%, 80%, 85%, 90%, 92.5%, 95%, 98%, 99%, 99.5%, 99.8%, 99.9%, 99.95%, or 99.99% of their nuclear DNA content derived from a *C. annuum* plant. The plants of the present invention may comprise about 0.2% to 25%, 0.5% to 25%, 1.0% to 25%, 2.0% to 25%, 5% to 25%, 7.5% to 25%, 10% to 25%, 15% to 25% or 20-25% of their nuclear DNA content derived from a *C. pubescens* plant.

Methods of the present invention also permit the preparation of an interspecific hybrid pepper plant resulting from a *C. annuum* and *C. pubescens* cross, or a part thereof, having a nuclear genome with, consisting of, consisting essentially of, or comprising nucleic acid sequences from *C. annuum* and *C. pubescens*. Alternatively, the interspecific hybrid pepper plant resulting from a *C. annuum* and *C. pubescens* cross, a part thereof, including a seed therefrom, can have a nuclear genome with, consisting of, consisting essentially of, or comprising nucleic acid sequences from *C. annuum*, nucleic acid sequences from *C. pubescens*, and one or more optional transgenes that have been introduced from a source other than a *Capsicum* species.

In one aspect, where an interspecific hybrid pepper plant resulting from a *C. annuum* and *C. pubescens* cross, a part thereof, including a seed therefrom, has a nuclear genome with, consisting essentially of, or comprising nucleic acid sequences from *C. annuum* and *C. pubescens*, the interspecific hybrid pepper plant, part thereof, including a seed therefrom will not have nucleic acid sequences that are unique to one or more other members of the *Capsicum* genus.

In another aspect where an interspecific hybrid pepper plant resulting from a *C. annuum* and *C. pubescens* cross, a part thereof, including a seed therefrom, has a nuclear genome with, consisting essentially of, or comprising nucleic acid sequences from *C. annuum*, nucleic acid sequences from *C. pubescens*, and one or more optional transgenes, the interspecific hybrid pepper plant, part thereof, including a seed therefrom will not have nucleic acids that are unique to another member of the *Capsicum* genus.

In one aspect of the invention, an interspecific F1 hybrid plant is a fertile interspecific *C. annuum* and *C. pubescens* hybrid plant, or a part thereof, comprising nucleic acid molecules derived from *C. annuum* and *C. pubescens*, where said fertile interspecific *C. annuum* and *C. pubescens* hybrid plant, or a part thereof is resistant for tobamovirus. In another aspect, an interspecific F1 hybrid plant is a fertile interspecific *C. annuum* and *C. pubescens* hybrid plant, or a part thereof, comprising nucleic acid molecules derived from *C. annuum* and *C. pubescens*, where said fertile interspecific *C. annuum* and *C. pubescens* hybrid plant, or a part thereof is resistant for tobamovirus and further comprises one or more traits selected from the group consisting of: resistance to geminivirus, resistance to tobamovirus, resistance to *Xanthomonas*, resistance to aphids, resistance to powdery mildew, ease of fruit shedding, cold tolerance, leaf hair, purple flower, purple style, purple anther purple filament, leaf wrinkle, black seed color, fruit color, thick fruit walls, flavor differences, and the clustering of seed-bearing placental tissue close to the stem of the fruit into *C. annuum* plants.

In one aspect of the invention, progeny of an interspecific F1 hybrid pepper plant produced by crossing *C. annuum* and *C. pubescens* (e.g., plants of a first, second, or third cross, or plants of a subsequent cross) or plants produced by bridge crosses, which may be fertile (non-sterile), may be prepared using only *Capsicum* species from the white flowered group (*C. annuum*, *C. baccatum*, *C. chacoense*, *C. chinense*, *C. frutescens*, *C. galapagoense*, *C. praetermissum*), and the purple flowered species *C. pubescens*. Such plants may be selfed one or more times, or crossed one or more times with *C. annuum* plants, *C. annuum* hybrids, or other members of the *Capsicum* genus, or hybrids thereof, including, *C. annuum*, *C. baccatum*, *C. chacoense*, *C. chinense*, *C. frutescens*, *C. galapagoense*, *C. praetermissum* and *C. pubescens*, that have been independently selected for each cross or combination of crosses to produce hybrid plants and seeds therefrom. Such plants may have no nuclear genetic material derived *C. eximium*, *C. tovarii*, or *C. cardenasii*. Alternatively, such plants, may have no nuclear DNA specific or unique to one or more plants selected from *C. cardenasii*, *C. eximium*, and *C. tovarii*.

Methods of the present invention also make possible the production of interspecific hybrids of a *C. annuum* plant bearing one or more introgressions from *C. pubescens* and one or more introgressions from a member of the *Capsicum* genus selected from the group consisting of: *C. chinense*, *C. baccatum*, *C. praetermissum*, *C. eximium* and *C. cardenasii*.

The skilled artisan will also recognize in light of the present invention that in this context a *C. annuum* plant bearing one or more introgressions refers to a plant whose nuclear genetic makeup is principally derived from *C. annuum*. In some aspects, greater than 50%, 60% or 75% of the nuclear genome of such plants is derived from *C. annuum*. In other aspects, greater than 80%, 85%, 90%, 95%, 97.5%, 98%, 99%, 99.5%, 99.8%, 99.9%, 99.95%, or 99.99% are derived from *C. annuum*.

The fraction of the genome that is derived from *C. pubescens* or *C. annuum* can be established by any method known in the art including, but not limited to, the detection of markers or sequencing to determine where introgressions have occurred.

EXAMPLES

Example 1

Direct Crossing of *C. annuum* and *C. pubescens*

Example 1a

Direct Crossing of *C. annuum* and *C. pubescens* using Emasculated Flowers of a *Capsicum annuum* plant as the Female Parent Interspecific hybrids of *Capsicum annuum* and *Capsicum pubescens* are obtained by in vivo pollination supported by embryo culture of the hybrid plants.

In order to produce the hybrids, flowers of a *C. annuum* parent plant are emasculated in early morning before anthers shed. The flowers are then pollinated with pollen of *C. pubescens* around 10 AM. One day post-pollination, the flowers are treated with naphthal acetic acid (NAA) by immersing the pollinated flowers in 200 mg/l solution of NAA in water. After the NAA solution has dried, the flowers are subjected to a second pollination with the pollen remaining from that applied the previous day.

A large number of such interspecific crosses produce small fruit that yield some seeds having underdeveloped embryos. When ripe, fruits that develop from the pollinated flowers are harvested and seed extraction and embryo rescue conducted under aseptic condition. Embryos are dissected from endosperms and cultured on Murashige & Skoog (MS) media till seedlings fully develop.

Example 1b

Direct Crossing of *C. annuum* and *C. pubescens* using Flowers of a *Capsicum annuum* Plant Cultured In Vitro as the Female Parent Interspecific hybrids of *Capsicum annuum* and *Capsicum pubescens* are obtained by in vitro propagation of flower tissue, in vitro pollination, and embryo culture of the hybrid plants.

In order to produce the hybrids, flower buds of the *C. annuum* parent are collected and sterilized with 3% $H_2O_2$ for 25 min, then rinsed with sterile water. The sterilized flower buds are plated onto MS media containing 0.05 mg/l of NAA, 0.2 mg/l of 6-benzylaminopurine (BAP), 3% sucrose, and 6.5 g/l of Phytagar, with a final pH of 5.7, and kept under continuous light overnight under a laminar flow hood. Each plate is covered with a lid without sealing. For pollination, fresh flowers of *C. pubescens* are collected in the early morning prior to flower opening and plated onto MS medium. Later in the day, when pollen of the male parent is shed, a whole anther is removed and used to pollinate the female flowers plated on MS media. Pollination is accomplished by touching the pollen-shedding anthers to the stigma of the cultured flowers. The plates are covered with their lids without sealing.

Pollinated flowers are kept under continuous light for 1 day until the wilting petal crowns are pushed up. The wilted petal crowns are removed and the ovaries are subcultured on MS media supplemented with 3% sucrose, 0.05 mg/l NAA and 0.2 mg/l 6-benzyladenine (BA). The plates are sealed with a flexible film, (e.g., PARAFILM®) and incubated in a growth room at 25+/−3° C., with a photoperiod 14 h until the fruit develops and ripens. Plates are periodically checked for contamination and embryos are subcultured to new media as necessary. Ripening fruit are opened and embryo rescue is done by dissecting the embryos out of their endosperms. Naked embryos are cultured on MS media with 3% sucrose and 6.5 g/l of Phytagar, final pH 5.7, in the absence of growth regulators to induce germination and seedling development.

Example 2

Characterization of *C. annuum*×*C. pubescens* F1 Progeny

Traits of the F1 progeny can evidence the successful crossing of *C. annuum* and *C. pubescens* plants. Traits such as the appearance/phenotype of the plant or pepper fruit, or the presence of genetic markers as outlined in Example 2, parts 2a and 2b distinguish successful crosses. The pollen fertility of interspecific F1 hybrids of *C. annuum*×*C. pubescens* are utilized and assessed as described in Example 2 part 2c.

Example 2a

Plant and Pepper Fruit Appearance/Phenotype

A variety of plant traits evidence the successful crossing of *C. annuum* and *C. pubescens*. Phenotypic traits selected from: geminivirus resistance, tobamovirus resistance, *Xanthomonas* resistance, ease of fruit shedding, cold tolerance, leaf hair, purple flower, purple style, purple anther filament, leaf wrinkle, black seed color, fruit color, fruit type, thick fruit walls, flavor differences, and the clustering of seed-bearing placental tissue close to the stem of the fruit may be used as indicators of successful cross breeding.

Figure 3:
FIG. 3 shows a color change associated with the formation of *C. annuum*×*C. pubescens* F1 hybrids. *C. annuum* flowers are white (left), *C. pubescens* flowers are purple, depicted as dark gray (right), and interspecific F1 hybrid flowers are light purple, depicted as light gray (center).

In one aspect, flower color also serves as a distinct marker for the F1 cross between *C. annuum* and *C. pubescens*. Plants of *C. annuum* have white flower whereas plants of *C. pubescens* have distinctly purple flowers. In contrast to either parent, the F1 hybrids have a light purple flower color. See FIG. 3 where the white flower of *C. annuum* is shown on the left, the light purple F1 hybrid flower is shown in the middle depicted as light gray, and the *C. pubescens* purple flower is shown on the right depicted as dark gray.

Figure 4:
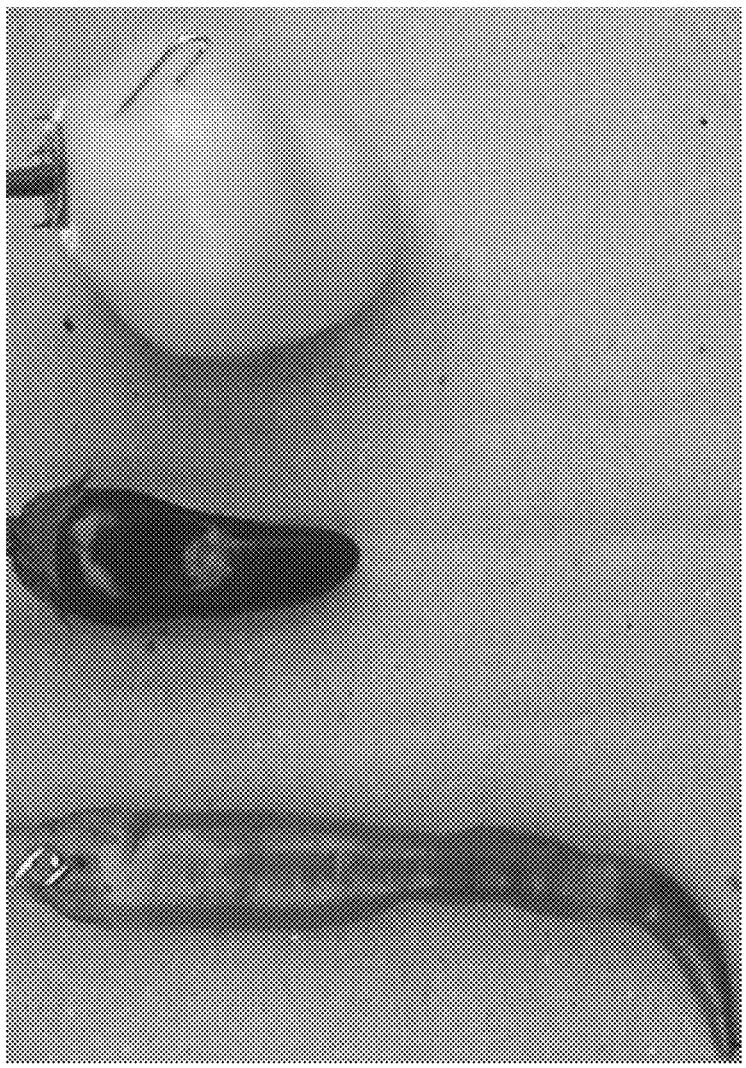
FIG. 4 shows a *C. annuum* female parent fruit (left), a *C. pubescens* male parent fruit, and the fruit of an interspecific F1 hybrid between the parents (center).

In another aspect, the shape or color of the mature fruit of F1 progeny resulting from a cross between *C. annuum* and *C. pubescens* is evidence formation of hybrid progeny depending upon the shape or color of the fruit of the *C. annuum* plant utilized in the cross. *C. pubescens* has a predominantly spherical shape and when crossed with varieties of *C. annuum* having a substantially different shape or color of the fruit from the resulting progeny can provide phenotypic evidence of the cross. See FIG. 4.

Example 2b

Genetic Markers for *C. annuum* and *C. pubescens*

Figure 5:
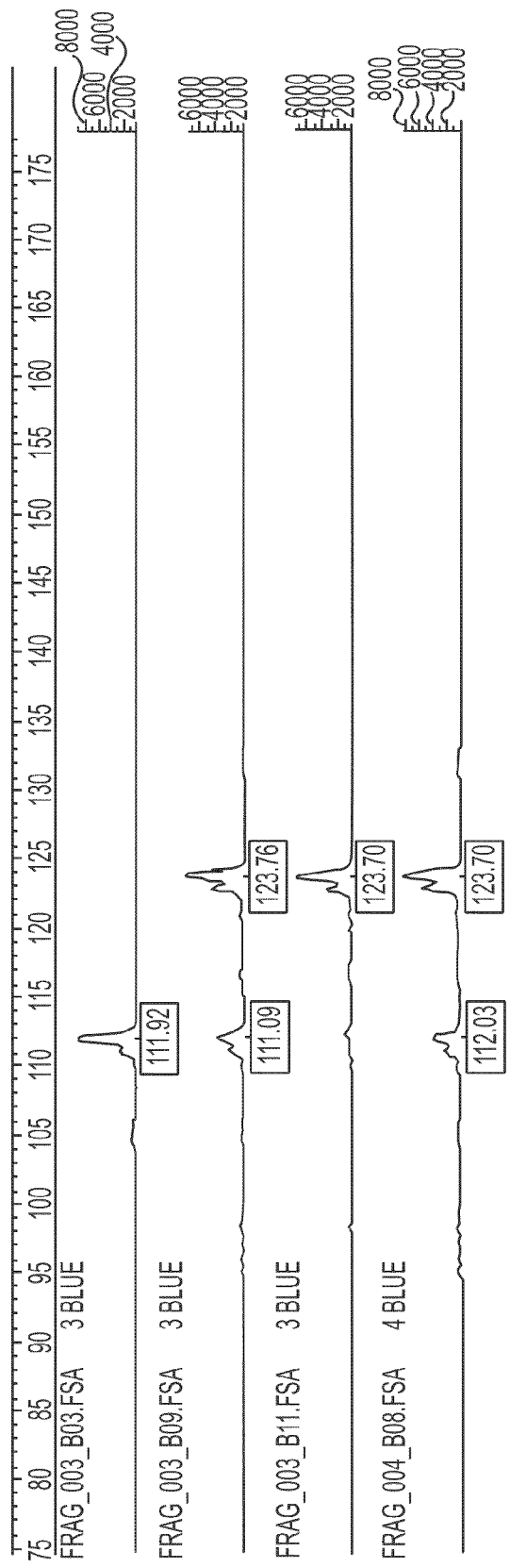
FIG. 5 shows profiles of Short Terminal Repeat (STR) marker SVS 3761 analysis of two interspecific hybrids and their parents. From top to bottom: Lane 1: *C. pubescens*; Lane 2: Interspecific hybrid (plant AP2); Lane 3: *C. annuum*; and Lane 4: Interspecific hybrid (plant AP1).
Figure 6:
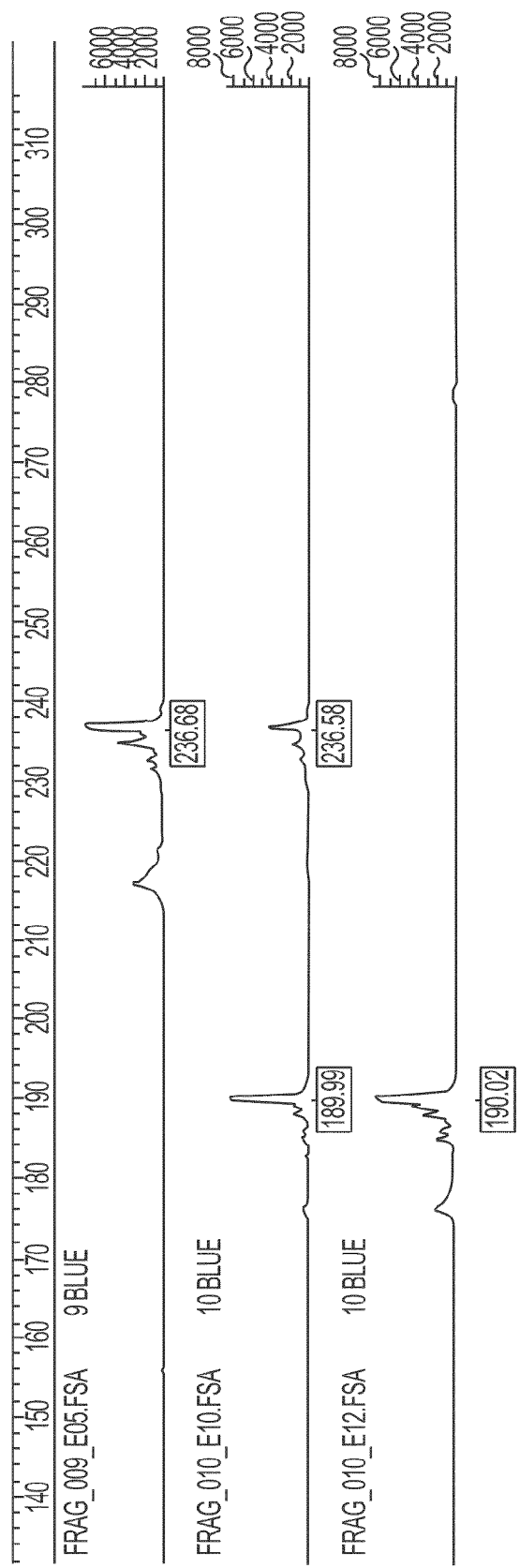
FIG. 6 shows profiles of STR marker SVS 2858 analysis of the interspecific hybrid AP3 and its parents. Top lane: *C. pubescens*; Center lane: interspecific hybrid (plant AP3); and Bottom lane: *C. annuum*.

Interspecific F1 progeny are developed from crossing *C. annuum* and *C. pubescens* are identified by the use of genetic markers including Short Tandem Repeats (STRs). The analyses of three interspecific hybrids using STR markers are shown in FIG. 5 and FIG. 6.

Repeats unique to the *C. annuum* lines and repeats unique to the *C. pubescens* lines employed in two interspecific crosses and are amplified from the nuclear DNA of the *C. annuum* parent lines, the *C. pubescens* parent lines, and interspecific F1 hybrids derived from crosses between those parent lines. The amplification products are separated on a gel, which is subsequently scanned. Lanes in which the genetic material of an interspecific F1 hybrid plant of *C. annuum* and *C. pubescens* is analyzed show the presence of both markers.

Example 2c

Pollen Fertility of *C. annuum* and *C. pubescens* Interspecific F1 Hybrids

Pollen fertility is determined by assessing the number of rounded pollen grains that are well stained by the chromosome stain acetocarmine. Rounded pollen represents normal pollen and serves as a surrogate measure of viable pollen, but the measure is not necessarily equal to viable pollen.

For the assessment of pollen fertility three flowers at anthesis stage are collected in a paper envelope and brought into the lab. A total of three anthers (one from each flower) are taken randomly from the flowers. The anthers are mashed in a drop of acetocarmine on a glass slide using fine tip forceps to release the pollen. The remaining mashed tissue is removed and a cover slip is placed on top of the stain drop. Rounded well stained pollen and shrunken faintly stained pollen (aborted) are counted, and the ratio of round pollen to total pollen is taken as a measure of pollen fertility.

Pollen of interspecific F1 hybrids of *C. annuum*×*C. pubescens* can be used to pollinate female *C. annuum* parents. Using the pollen from the hybrid it is possible to prepare first and second backcross plants (BC1 and BC2, respectively) using the *C. annuum* parent as the recurrent parent in the backcross (see Scheme 1 as depicted in FIG. 1). In addition to backcrossing with a recurrent parent, BC1 plants are selfed to prepare BC1S1 plants (see Scheme 1 as depicted in FIG. 1) and BC1S2 plants (not shown). These plants are employed to introgress traits from *C. pubescens* into *C. annuum*. Progeny tend to have low pollen fertility, which ranges from 0.0% to 0.5%.

The pollen fertility of interspecific F1 hybrids of *C. pubescens* and *C. annuum* is shown in Tables 1a and 1b. The two pollinations in Table 1a, are from different seasons.

the plant designated CP1047, and plants propagated from it, have better pollen fertility than other F1 plants in a range of environments.

TABLE 1b

Pollen fertility of interspecific F1 hybrids of *C. annuum* and *C. pubescens*

| F1 | % Fertility | Pedigree |
|---|---|---|
| CP1350 | 0.1 | CP367 × CP348 = P3850 × Pi235047#1 |
| CP980a | 0.1 | CP369 × CP348 = P3117 × Pi235047#1 |
| CP1324 | 0.1 | CP331 × CP358 = PX1141-0025 × Pi235047#1 |
| CP1323 | 0.1 | CP331 × CP358 = PX1141-0025 × Pi235047#1 |
| CP 980 | 0.5 | CP369 × CP348 = P3117 × Pi235047#1 |
| CP1046 | 0.7 | CP371 × CP349 = P3117 × pi23504733#1 |
| CP1047 | 4.1 | CP367 × CP348 = P3850 × CP235047#1 |
| CP1352 ‡ | 4.8 | |
| CP1352 ‡ | 8.7 | |
| CP1352 ‡ | 9.5 | |
| CP1352 ‡ | 13.2 | |
| CP1871 ‡ | 0.7 | |
| CP1874 ‡ | 1.0 | |
| CP1871 ‡ | 1.1 | |
| CP1875 ‡ | 1.4 | |
| CP1875 ‡ | 1.5 | |
| CP1873 ‡ | 1.7 | |
| CP1872 ‡ | 2.4 | |

‡ Indicates the F1 plant is asexually propagated from interspecific F1 hybrid plant CP1047. The individual propagated plants are grown under a variety of conditions and pollen fertility counts taken at different ages.

Interspecific F1 hybrids are used to prepare subsequent crosses including plants of the first generation backcross (BC1). Most *C. annuum* flowers that pollinate with interspecific F1 pollen fail to develop into fruit and are aborted.

The pollen fertility measurements of BC1 progeny made by backcrossing interspecific F1 hybrids of *C. annuum*×*C. pubescens* with *C. annuum* (i.e., ann(annxpub)) are shown in Table 2a.

TABLE 1a

Pollen fertility of interspecific F1 hybrids of *C. annuum* and *C. pubescens*

| | | | May 24, 2007 | | | Jan. 8, 2007 | | | |
|---|---|---|---|---|---|---|---|---|---|
| ID | ♀ C. ann | ♂ C. pub | Round † | Aborted | % fertile (a) | Round † | Aborted | % fertile (b) | Ratio b/a |
| CP977 | CP371 | CP349 | 0 | 2307 | 0 | 3 | 1540 | 0.195 | nd |
| CP978 | CP370 | CP348 | 0 | 3045 | 0 | 4 | 1880 | 0.213 | nd |
| CP 979 | CP369 | CP348 | 0 | 3579 | 0 | 7 | 2570 | 0.272 | nd |
| CP 980 | CP369 | CP348 | 1 | 1053 | 0.0949 | 7 | 1386 | 0.503 | 5.3 |
| CP1046 | CP371 | CP349 | 8 | 1680 | 0.4739 | 15 | 2258 | 0.660 | 1.4 |
| CP1047 | CP367 | CP348 | 2 | 2674 | 0.0747 | 12 | 2570 | 0.465 | 6.2 |
| CP1350 | CP367 | CP348 | 1 | 2305 | 0.0434 | 4 | 1795 | 0.222 | 5.1 |
| CP1343 | CP521 | CP362 | 0 | 2462 | 0 | nd ‡ | nd ‡ | nd ‡ | nd ‡ |
| Total | | | 12 | 19105 | 0.0628 | 52 | 13999 | 0.3715 | 5.91561 |

‡ (nd) not determined
† Pollen with normal appearance when stained with acetocarmine.

Pollen fertility and pedigree of some of the interspecific F1 hybrids listed in Table 1a and some additional F1 hybrids are shown in Table 1b. Plants CP1352, CP1871, CP1872, CP1873, CP1874, and CP1875 are each taken from different cuttings of the plant designated CP1047 made at different times. Cuttings are propagated into plants under different conditions and the pollen fertility of those plants is assessed at different times (cool and warm season), at different plant ages, and growth in different greenhouses. Data indicate that The pollen fertility of two interspecific F1 hybrids of *C. annuum*×*C. pubescens*, two additional BC1 plants not presented in Table 2a, and several BC2 and BC1S1 plants are shown in Table 2b. The BC2 plants are prepared by backcrossing interspecific F1 hybrids of *C. annuum*×*C. pubescens* to *C. annuum* two times (i.e., ann(ann(annxpub)) ). The BC1S1 plants are prepared by selfing BC1 plants. The data provide evidence that specific genetic combinations can improve pollen fertility.

TABLE 2a

Pollen Fertility of BC1 progeny ((*C. annuum* × *C. pubescens*) backcrossed to *C. annuum*)

| ID | % Fertility |
|---|---|
| CP1507 | 4.0 |
| CP1508 | 48.5 |
| CP1509 | 10.1 |
| CP1700 | 4.2 |
| CP1711 | 4.9 |
| CP1712 | 0.1 |
| CP1732 | 4.4 |
| CP1738 | 60.8 |
| CP1739 | 0.0 |
| CP1742 | 23.4 |
| CP1743 | 35.5 |
| CP1744 | 0.0 |
| CP1992 | 1.5 |

Example 3
Preparation of Pepper Hybrids with Improved Pollen Fertility

Hybrids having higher pollen fertility than the interspecific F1 hybrids prepared by crossing *C. annuum* and *C. pubescens* are prepared by crossing the BC1, BC2 or BC1S1 plants described above in Example 2c with *C. pubescens*. For the crosses with *C. pubescens*, BC1, BC2 or BC1S1 plants with the highest pollen fertility are selected. Some of the resulting hybrids, denoted plants of a second cross in Scheme 1 as depicted in FIG. 1, can have higher pollen fertility and are used in the preparation of backcrosses with *C. annuum* plants as the recurrent parent to form subsequent generations of plants that are used in the selection of traits introgressed from *C. pubescens* into *C. annuum*.

The pollen fertility of the plants of a second cross indicted in Table 3 as "Alternate F1s," made by crossing the BC1, BC2 and BC1S2 hybrids prepared as discussed in Example 2c with *C. pubescens*, are shown in Table 3.

TABLE 2b

Pollen Fertility in Crosses of the Interspecific F1 Hybrids

| ID | Pedigree | | Generation/Description | Round † | Aborted | Total | % Fertile |
|---|---|---|---|---|---|---|---|
| CP980 | P3117 ♀ × C. ann. | PI235047#1 ♂ C. pub. | Interspecific F1 | 7 | 1386 | 1393 | 0.005 |
| CP1046 | P3850 ♀ × C. ann. | PI235047#1 ♂ C. pub. | Interspecific F1 | 15 | 2258 | 2273 | 0.007 |
| CP449 | P3850 ♀ × C. ann. | (P31177 × P31170) ♂ C. pub. | F1 crossed to a ♀ C. ann. plant | 275 | 71 | 346 | 0.79 |
| CP814 | P3850 ♀ × C. ann. | P3850(P3117 × PI235047) | F1 crossed to C. ann. plants twice | 133 | 97 | 230 | 0.58 |
| CP822 | P3850 ♀ × C. ann. | P3850(P3117 × PI235047) | F1 crossed to C. ann. plants twice | 85 | 105 | 190 | 0.45 |
| CP823 | P3850 ♀ × C. ann. | P3850(P3117 × PI235047) | F1 crossed to C. ann. plants twice | 217 | 33 | 250 | 0.87 |
| CP974 | P3117 ♀ × C. ann. | P3850(P3117 × PI235047) | F1 crossed to C. ann. plants twice | 256 | 394 | 650 | 0.39 |
| CP975 | P3117 ♀ × C. ann. | P3850(P3117 × PI235047) | F1 crossed to C. ann. plants twice | 139 | 339 | 478 | 0.29 |
| CP976 | P3850 ♀ × C. ann. | P3850(P3117 × PI235047) | F1 crossed to C. ann. plants twice | 203 | 9 | 212 | 0.96 |
| CP913 | P3850 (P3117 × PI235047) selfed | | F1 crossed to C. ann. and selfed | 113 | 291 | 404 | 0.28 |
| CP906 | P3850 (P3117 × PI235047) selfed | | F1 crossed to C. ann. and selfed | 84 | 150 | 234 | 0.36 |
| CP907 | P3850 (P3117 × PI235047) selfed | | F1 crossed to C. ann. and selfed | 128 | 466 | 594 | 0.22 |
| CP908 | P3850 (P3117 × PI235047) selfed | | F1 crossed to C. ann. and selfed | 172 | 182 | 354 | 0.49 |
| CP909 | P3850 (P3117 × PI235047) selfed | | F1 crossed to C. ann. and selfed | 73 | 169 | 242 | 0.30 |
| CP910 | P3850 (P3117 × PI235047) selfed | | F1 crossed to C. ann. and selfed | 30 | 319 | 349 | 0.09 |
| CP911 | P3850 (P3117 × PI235047) selfed | | F1 crossed to C. ann. and selfed | 233 | 117 | 350 | 0.67 |

† Pollen with normal when appearance stained with acetocarmine.

P3117 is PBC 615 Matikas, from the AVRDC (Asian Vegetable Research and Development Center) in Taiwan, and is publicly available.

P3850 is PBC 142 PANT C-1 from the AVRDC in Taiwan, and is publicly available.

TABLE 3

Pollen fertility of plants of crosses

| ID | % Fertility | Parents | Parent pedigree | Alternate F1s |
|---|---|---|---|---|
| CP1753 | 0.0 | CP74 × CP349 | BC1 × pub | [(ann(ann × pub)]pub |
| CP1757 | 0.8 | CP75 × CP348 | BC1 × pub | [(ann(ann × pub)]pub |
| CP1757 | 1.8 | CP75 × CP348 | BC1 × pub | [(ann(ann × pub)]pub |
| CP1769 | 1.2 | CP1538 × CP349 | BC1 × pub | [(ann(ann × pub)]pub |
| CP1789 | 0.1 | CP913 × CP349 | BC1S1 × pub | [ann(ann × pub)] self1///pub |
| CP1798 | 0.7 | CP913 × CP349 | BC1S1 × pub | [ann(ann × pub)] self1///pub |
| CP1815 | 0.2 | CP913 × CP349 | BC1S1 × pub | [ann(ann × pub)] self1///pub |
| CP1817 | 0.2 | CP913 × CP349 | BC1S1 × pub | [ann(ann × pub)] self1///pub |
| CP1822 | 2.7 | CP913 × CP349 | BC1S1 × pub | [ann(ann × pub)] self1///pub |
| CP1822 | 0.6 | CP913 × CP349 | BC1S1 × pub | [ann(ann × pub)] self1///pub |
| CP1826 | 0.1 | CP976CP347 | BC2 × pub | [ann///ann//(ann/pub)////pub |
| CP1826 | 0.5 | CP976CP347 | BC2 × pub | [ann///ann//(ann/pub)////pub |
| CP1827 | 0.2 | CP976CP347 | BC2 × pub | [ann///ann//(ann/pub)////pub |

While the pollen fertility of the plants indicated in Table 3 may not appear as high as that of the BC1 plants of Table 2a, the genetic complement of these plants makes them more desirable for the introduction of traits into *C. annuum* as they display improved ability to cross with other members of the *Capsicum* genus, particularly *C. annuum* plants and hybrids.

Example 4

Preparation of Interspecific Hybrids of *C. annuum* and *C. pubescens* using a Bridging Species Interspecific hybrid pepper plants are prepared by crossing *C. pubescens* or *C. annuum* with another *Capsicum* species that acts as a bridge and facilitates the movement of traits from *C. pubescens* to *C. annuum*.

Where the bridging species is to be crossed with *C. annuum* prior to any cross with *C. pubescens*, a first cross is made between *C. annuum* plants and a member of the *Capsicum* genus selected from the group consisting of: *C. chinense, C. baccatum, C. praetermissum, C. eximium,* and *C. frutescens*, and the progeny of the first cross are subsequently employed in a second cross with *C. pubescens* to form hybrids between *C. annuum* and *C. pubescens*. Alternatively, a first cross between *C. cardenasii* and *C. pubescens* can be made and the progeny of that cross can be crossed with *C. annuum*.

Results of some crosses using bridging species are given in Table 4. The species in parenthesis are those employed in the first cross whose progeny are employed in the subsequent second cross. The species separated by the double slashes "//" represents the other species used in the second cross.

TABLE 4

Bridge crosses

| Bridge Cross | Fruit development | # Seeds | # Embryos |
|---|---|---|---|
| (annuum/chinense)//pubescens | ++ | 29 | 13 |
| (eximium/annuum)//pubescens | ++ | 1 | 1 |
| (praetermissum/annuum)//pubescens | +++ | 9 | 0 |
| (annuum/frutescens)//pubescens † | + | 42 | 0 |
| annuum//(cardenasii/pubescens) | +++ | 20 | 3 |

+ indicates approximately 25% of the pollinations developed into fruit
++ indicates approximately 50% of the pollinations developed into fruit
+++ indicates approximately 75% of the pollinations developed into fruit
++++ indicates approximately 100% of the pollinations developed into fruit
† Crosses between *C. annuum* and *C. frutescens* do not require auxin or cytokinin treatment, crosses between the F1 progeny of *C. annuum* and *C. frutescens* and *C. pubescens* require treatment of the flowers with an auxin (e.g., NAA) prior to pollination by *C. pubescens*.

Embryos from the seeds of the secondary cross are harvested from the seeds of ripe fruit and cultured on MS media as described in Example 1 to obtain plants.

Hybrid pepper plants obtained from a cross between *C. annuum* and a bridging species are then crossed to *C. pubescens*, and then crossed to *C. annuum* plants one or more times to obtain subsequent generations of *C. annuum* plants bearing one or more introgressions from *C. pubescens*, one or more introgressions from a bridging species, one or more introgressions from *C. pubescens* and a bridging species. Hybrid pepper plants obtained from a cross between *C. pubescens* and a bridging species are then crossed to *C. annuum*, and then crossed to *C. pubescens* plants one or more times and then crossed back to *C. annuum* to obtain subsequent generations of *C. annuum* plants bearing one or more introgressions from *C. pubescens*, one or more introgressions from a bridging species, one or more introgressions from *C. pubescens* and a bridging species.

Example 5

Determination of Resistance to Geminivirus

Individual plants are grown in an artificial soil mix in a greenhouse. When plants are at the desired stage of growth they are inoculated with a geminivirus culture (e.g., by atomizing or "painting" a suspension of the viral stock solution on the surface of one or more of the leaves). At least one leaf of the plant is abraded with carborundum powder prior to inoculating the leaves. The plants are maintained in a greenhouse subject to ambient humidity and a temperature of about 23° C. to about 32° C. until disease development is assessed. Susceptible plants are grown and treated identically to act as controls.

Of the plants exposed to geminivirus infection, some do not show any signs of infection, whereas others show delayed symptoms of infection, or a reduced severity of symptoms (compared to susceptible control plants). Compared to control plants, hybrid plants have fewer individuals showing signs of geminivirus infection; of those plants showing signs of geminivirus infection, the symptoms are delayed compared to control plants and are less severe compared to control plants or symptoms are delayed compared to control plants or are less severe compared to control plants.

Plants grown in an open field and exposed to the indigenous species of geminivirus present or the plants may be infected with a desired strain of geminivirus. Field trials are performed in Salama, Guatemala to take advantage of the high-Geminivirus-pressure environment existing in this location. Plants from two BC1F2 generation crosses, two BC2F2 generation crosses and one F2 generation of an annuum/bridge cross are planted. *C. pubescens* plants are used as the resistant control. *C. annuum* plants (including all annuum parents in these pedigrees) are planted in the field as the susceptible controls. High natural disease pressure results in 100% infection on the susceptible controls with characteristic symptoms including leaf distortion, leaf curling, severe stunting, reduced leaf size, and in severe cases, reduction in flower and fruit production, such as number and size of flower, fruit or flower and fruit. Resistance is observed in 2 of 38 BC1F2 plants, 5 of 215 BC2F2 plants and in 1 of 40 annuum/Bridge F2 plants. Resistant plants show vigorous growth and no signs of infection. Open field geminivirus resistant lines are identified in Table 5.

TABLE 5

Exemplary open field geminivirus resistant lines

| Line | Designation | Parental lineage | Line lineage |
|---|---|---|---|
| BC1F2 line 1 | 09GP2518 = CP2259 | ann//ann/pub | CP1653//CP1352 |
| | | | CP1653//CP367/CP348 |
| BC1F2 line 2 | 09GP2518 = CP2260 | ann//ann/pub | CP2039//CP1352 |
| | | | CP2039//CP367/CP348 |
| BC2F2 line 1 | 09GP2509 = CP2239 | ann//ann/pub///ann | CP1738/CP328 |
| | | | CP1441/CP1046/CP328 |
| | | | CP1441//CP371/CP349///CP328 |
| BC2F2 line 1 | 09GP2509 = CP2246 | ann//ann/pub///ann | CP1738/CP328 |
| | | | CP1441/CP1046/CP328 |
| | | | CP1441//CP371/CP349///CP328 |
| ann/Bridge | 09GP2522 = CP2264 | (ann///ann//car/pub)F2 | CP327/CP1782 |
| | | | CP327//CP328/CP1456 |
| | | | CP327///CP328//CP457/CP347 |

Example 6

Determination of Resistance to *Xanthomonas*

Individual plants are grown in an artificial soil mix in a greenhouse. When plants are at the desired stage of growth they are inoculated with a culture of the bacterial leaf spot pathogen, *Xanthomonas* (e.g., *Xanthomonas campestris*) by atomizing a suspension of the bacteria over the leaf surfaces of the plants. The plants are maintained in a closed chamber for 48 hours with supplemental misting supplied by cool-mist foggers. The plants are then maintained in a greenhouse subject to ambient humidity and a temperature of about 23° C. to about 32° C. until disease development is assessed. Susceptible plants are grown and treated identically to act as controls.

Of the plants exposed to *Xanthomonas*, some do not show any signs of infection whereas others will show delayed symptoms of infection, or a reduced severity of symptoms (compared to susceptible control plants). Compared to control plants, hybrid plants have fewer individuals showing signs of *Xanthomonas* infection; of those plants showing signs of *Xanthomonas* infection, the symptoms are delayed compared to control plants and are less severe compared to control plants or symptoms are delayed compared to control plants or are less severe compared to control plants.

Example 7

Determination of Resistance to Tobamovirus

Pepper plants from the species *C. pubescens* are the source of resistance to strains of Tobamovirus and can be a source for introducting tobamovirus resistance into *C. annuum* species using the described breeding methods. The resistance of *C. pubescens* lines are assessed as described in Example 7, part 7e.

Example 7a

Determination of Resistance to Tobamovirus Strain $P_0$

Individual plants are grown in an artificial soil mix in a greenhouse. An inoculum of Tobamovirus $P_0$ is prepared by infecting host Golden Cal Wonder Pepper plants with isolate TMV-$P_0$ (or $L_1$) at the 4 true leaf stage. The host plant is inoculated by scraping the tops of two true leaves with a finger dipped in inoculum mixed with a small amount of diatomaceous earth (as an abrasive) and then rinsed with water. Leaves are picked and stored, undried, in the freezer until needed. To inoculate test plants, an inoculum is prepared by suspending 1 g of frozen leaf tissue in 50 ml. of phosphate buffer (0.1M, pH 7). Test plants are inoculated when plants have 2-4 true leaves by gently scraping the tops of two true leaves with a finger dipped in inoculum mixed with a small amount of diatomaceous earth (as an abrasive). The leaves are then rinsed with water. Plants are grown in flats on a greenhouse bench at about 18° C. to about 29° C. During winter months supplemental artificial light is provided to allow expression of the fully hypersensitive reaction to express fully. Susceptible Golden Cal Wonder Pepper plants and resistant Yolo Wonder B plants are grown and treated identically to act as controls. Four to 9 days after inoculation when plants have 3 to 4 true leaves, disease development is assessed.

Of the plants exposed to Tobamovirus strain $P_0$, some do not show any signs of infection whereas others show delayed symptoms of infection, or a reduced severity of symptoms (compared to susceptible Golden Cal Wonder Pepper and Yolo Wonder B plants). Plants of *C. pubescens* plant line PI235047#1 are resistant to Tobamovirus $P_0$.

Example 7b

Determination of Resistance to Tobamovirus Strain $P_1$

Individual plants are grown in an artificial soil mix in a greenhouse. An inoculum of Tobamovirus $P_1$ is prepared by infecting host Yolo Wonder B pepper plants with isolate TMV-$P_1$ (or $L_2$) at the 4 true leaf stage. The host plant is inoculated by scraping the tops of two true leaves with a finger dipped in inoculum mixed with a small amount of diatomaceous earth (as an abrasive) and then rinsed with water. Leaves are picked and stored, undried, in the freezer until needed. To inoculate test plants, an inoculum is prepared by suspending 1 g of frozen leaf tissue in 50 ml. of phosphate buffer (0.1M, pH 7). Test plants are inoculated when plants have 2-4 true leaves by gently scraping the tops of two true leaves with a finger dipped in inoculum mixed with a small amount of diatomaceous earth (as an abrasive). The leaves are then rinsed with water. Plants are grown in flats on a greenhouse bench at about 18° C. to about 29° C. During winter months supplemental artificial light is provided to allow expression of the fully hypersensitive reaction to express fully. Susceptible Yolo B Wonder pepper plants and resistant TABASCO® plants are grown and treated identically to act as controls. Seven to 14 days after inoculation when plants have 3 to 4 true leaves, disease development is assessed.

Of the plants exposed to Tobamovirus strain $P_1$, some do not show any signs of infection whereas others show delayed symptoms of infection, or a reduced severity of symptoms (compared to susceptible Yolo B Wonder control plants). Plants of *C. pubescens* plant line PI235047#1 are resistant to Tobamovirus $P_1$.

Example 7c

Determination of Resistance to Tobamovirus strain $P_{1.2}$

Individual plants are grown in an artificial soil mix in a greenhouse. An inoculum of Tobamovirus $P_{1.2}$ is prepared by infecting host Yolo Wonder B pepper plants with isolate TMV-$P_{1.2}$ (or $L_3$) at the 4 true leaf stage. The host plant is inoculated by scraping the tops of two true leaves with a finger dipped in inoculum mixed with a small amount of diatomaceous earth (as an abrasive) and then rinsed with water. Leaves are picked and stored, undried, in the freezer until needed. To inoculate test plants, an inoculum is prepared by suspending 1 g of frozen leaf tissue in 50 ml. of phosphate buffer (0.1M, pH 7). Test plants are inoculated when plants have 2-4 true leaves by gently scraping the tops of two true leaves with a finger dipped in inoculum mixed with a small amount of diatomaceous earth (as an abrasive). The leaves are then rinsed with water. Plants are grown in flats on a greenhouse bench at about 18° C. to about 29° C. During winter months supplemental artificial light is provided to allow expression of the fully hypersensitive reaction to express fully. Susceptible Yolo B Wonder, Tabasco and Golden Cal Wonder pepper plants and resistant Novia and PI159236 pepper plants are grown and treated identically to act as controls.

Seven to 14 days after inoculation when plants have 3 to 4 true leaves, disease development is assessed.

Of the plants exposed to Tobamovirus strain $P_{1.2}$, some do not show any signs of infection whereas others show delayed symptoms of infection, or a reduced severity of symptoms (compared to susceptible control Yolo B Wonder, Tabasco and Golden Cal Wonder plants). Plants of *C. pubescens* plant line PI235047#1 are observed to be susceptible to Tobamovirus $P_{1.2}$

Example 7d

Determination of Resistance to Tobamovirus Strain $P_{1.2.3}$

Individual plants are grown in an artificial soil mix in a greenhouse. An inoculum of Tobamovirus $P_{1.2.3}$ is prepared by infecting host Yolo Wonder B pepper plants with isolate TMV-$P_{1.2.3}$ (or $L_4$ or CapMV) at the 4 true leaf stage. The host plant is inoculated by scraping the tops of two true leaves with a finger dipped in inoculum mixed with a small amount of diatomaceous earth (as an abrasive) and then rinsed with water. Leaves are picked and stored, undried, in the freezer until needed. To inoculate test plants, an inoculum is prepared by suspending 1 g of frozen leaf tissue in 50 ml. of phosphate buffer (0.1M, pH 7). Test plants are inoculated when plants have 2-4 true leaves by gently scraping the tops of two true leaves with a finger dipped in inoculum mixed with a small amount of diatomaceous earth (as an abrasive). The leaves are then rinsed with water. Plants are grown in flats on a greenhouse bench at about 18° C. to about 29° C. During winter months supplemental artificial light is provided to allow expression of the fully hypersensitive reaction to express fully. Susceptible Yolo B Wonder and Novia pepper plants and resistant CapMVR pepper plants are grown and treated identically to act as controls. Seven to 14 days after inoculation when plants have 3 to 4 true leaves, disease development is assessed.

Of the plants exposed to Tobamovirus strain $P_{1.2.3}$, some do not show any signs of infection whereas others show delayed symptoms of infection, or a reduced severity of symptoms (compared to susceptible control Yolo B Wonder and Novia plants). Plants of *C. pubescens* plant line PI235047#1 are observed to be resistant to Tobamovirus $P_{1.2.3}$.

Example 7e

Resistance to Tobamovirus in *C. pubescens* Lines

Tobamovirus resistance is observed in *C. pubescens* lines PI235047 and P18. Resistance is determined using the methods of Examples 7a-7d. The Tobamovirus resistance results are shown in Table 6.

TABLE 6

Tobamovirus resistance in *C. pubescens* lines

| Line | *C. pubescens* Line | TMV Race | # of Seeds to Plant | R‡ | S* | Results % R |
|---|---|---|---|---|---|---|
| CP 3265 | PI235047#1 | P0 (L1) | 25 | 10 | 0 | 100.00 |
| Golden Cal Wonder | n/a | P0 (L1) | 60 | 0 | 50 | 0.00 |
| Yolo Wonder B | n/a | P0 (L1) | 60 | 58 | 0 | 100.00 |
| CP 3266 | PI235047#1 | P1 (L2) | 30 | 10 | 0 | 100.00 |
| Yolo Wonder B | n/a | P1 (L2) | 30 | 0 | 30 | 0.00 |
| Tobasco | n/a | P1 (L2) | 30 | 1 | 0 | 100.00 |
| PI 152225 | n/a | P1 (L2) | 30 | 30 | 0 | 100.00 |
| CP 3266 | PI235047#1 | P1.2 (L3) | 25 | 0 | 18 | 0.00 |

TABLE 6-continued

Tobamovirus resistance in *C. pubescens* lines

| Line | C. pubescens Line | TMV Race | # of Seeds to Plant | R‡ | S* | Results % R |
|---|---|---|---|---|---|---|
| Yolo Wonder B | n/a | P1.2 (L3) | 30 | 0 | 30 | 0.00 |
| Tabasco | n/a | P1.2 (L3) | 30 | 0 | 15 | 0.00 |
| Golden Cal Wonder | n/a | P1.2 (L3) | 30 | 0 | 30 | 0.00 |
| Novia | n/a | P1.2 (L3) | 30 | 30 | 0 | 100.00 |
| PI 152225 | n/a | P1.2 (L3) | 30 | 30 | 0 | 100.00 |
| CP 3267 | PI235047#1 | P1.2.3 (L4) | 30 | 22 | 0 | 100.00 |
| Yolo Wonder B | n/a | P1.2.3 (L4) | 30 | 0 | 29 | 0.00 |
| Novia | n/a | P1.2.3 (L4) | 30 | 0 | 29 | 0.00 |
| CapMVR | n/a | P1.2.3 (L4) | 30 | 28 | 0 | 100.00 |

†plants did not germinate in the test planting
‡Hypersensitive Reaction
*No Hypersensitive Reaction
n/a: *C. annuum* species

What is claimed is:

1. A method of producing a fertile interspecific $F_1$ hybrid pepper plant comprising the steps of:
   (a) pollinating a male sterile flower of a *Capsicum annuum* parent selected from a *C. annuum* plant or a *C. annuum* hybrid with pollen from a *Capsicum pubescens* plant or *C. pubescens* hybrid to form a pollinated flower;
   (b) treating the pollinated flower with an auxin compound;
   (c) growing the *C. annuum* parent until the pollinated flower develops into a fruit bearing a seed;
   (d) harvesting the fruit bearing a seed that develops from the pollinated flower; and
   (e) rescuing embryonic tissue from the seed of the fruit to produce a fertile interspecific $F_1$ hybrid pepper plant;
   wherein said fertile interspecific $F_1$ hybrid plant has no nuclear genetic material unique to *Capsicum eximium* and does not have a *C. eximium* plant as an ancestor.

2. A fertile interspecific hybrid pepper plant, or a part thereof, produced by the method of claim 1, wherein said fertile interspecific $F_1$ hybrid plant has no nuclear genetic material unique to *Capsicum eximium* and does not have a *C. eximium* plant as an ancestor.

3. The fertile interspecific hybrid pepper plant, or the part thereof, of claim 2, wherein said fertile interspecific hybrid pepper plant has one or more traits selected from the group consisting of resistance to geminivirus, resistance to tobamovirus, resistance to *Xanthomonas*, resistance to aphids, resistance to powdery mildew, ease of fruit shedding, cold tolerance, purple flower, purple style, purple anther, purple filament, leaf wrinkle, black seed color, thick fruit walls, and the clustering of seed-bearing placental tissue close to the stem of the fruit.

4. The fertile interspecific hybrid pepper plant, or the part thereof, of claim 2, wherein said fertile interspecific hybrid pepper plant produces a sweet pepper fruit, a mild pepper fruit, a medium pepper fruit, a hot pepper fruit, or a very hot pepper fruit; wherein said pepper fruit has a shape selected from the group consisting of block, pointed and round; and wherein said pepper fruit has a color selected from the group consisting of green, red, yellow, orange, purple, brown and white.

5. The fertile interspecific hybrid pepper plant, or the part thereof, of claim 2 comprising nuclear DNA derived from a *C. pubescens* plant wherein the amount of said nuclear DNA is selected from the group consisting of about 0.2%, 0.5%, 1%, 2%, 5%, 7.5%, 10%, 15%, 20%, and 25%.

6. The fertile interspecific hybrid pepper plant, or the part thereof, of claim 2, wherein said part comprises one or more cells of a plant part selected from the group consisting of a leaf, pollen, an embryo, a root, a root tip, an anther, a flower, and a fruit.

7. The fertile interspecific hybrid pepper plant, or the part thereof, of claim 6, wherein said one or more cells are a culture of regenerable cells.

8. A method of producing a fertile interspecific $F_1$ hybrid pepper plant comprising the steps of:
   (a) culturing a flower bud of a *C. annuum* parent selected from a *C. annuum* plant or *C. annuum* hybrid to obtain a *C. annuum* flower;
   (b) pollinating said *C. annuum* flower with pollen from a *C. pubescens* plant or a *C. pubescens* hybrid to form a pollinated flower;
   (c) removing an ovary from said pollinated flower and subculturing said ovary in the presence of an auxin compound and a cytokinin compound;
   (d) maintaining said subcultured ovary until a fruit bearing a seed develops; and
   (e) rescuing immature embryo tissue from said seed of said fruit to produce a fertile interspecific $F_1$ hybrid pepper plant;
   wherein said fertile interspecific $F_1$ hybrid plant has no nuclear genetic material unique to *Capsicum eximium* and does not have a *C. eximium* plant as an ancestor.

9. A fertile interspecific hybrid pepper plant, or a part thereof, produced by the method of claim 8, wherein said fertile interspecific $F_1$ hybrid plant has no nuclear genetic material unique to *Capsicum eximium* and does not have a *C. eximium* plant as an ancestor.

10. The fertile interspecific hybrid pepper plant, or the part thereof, of claim 9, wherein said fertile interspecific hybrid pepper plant has one or more traits selected from the group consisting of resistance to geminivirus, resistance to tobamovirus, resistance to *Xanthomonas*, resistance to aphids, resistance to powdery mildew, ease of fruit shedding, cold tolerance, purple flower, purple style, purple anther, purple filament, leaf wrinkle, black seed color, thick fruit walls, and the clustering of seed-bearing placental tissue close to the stem of the fruit.

11. The fertile interspecific hybrid pepper plant, or the part thereof, of claim 9, wherein said fertile interspecific hybrid pepper plant produces a sweet pepper fruit, a mild pepper fruit, a medium pepper fruit, a hot pepper fruit, or a very hot pepper fruit; wherein said pepper fruit has a shape selected from the group consisting of block, pointed and round; and wherein said pepper fruit has a color selected from the group consisting of green, red, yellow, orange, purple, brown and white.

12. The fertile interspecific hybrid pepper plant, or the part thereof, of claim 9 comprising nuclear DNA derived from a *C. pubescens* plant wherein the amount of said nuclear DNA is selected from the group consisting of about 0.2%, 0.5%, 1%, 2%, 5%, 7.5%, 10%, 15%, 20%, and 25%.

13. The fertile interspecific hybrid pepper plant, or the part thereof, of claim 9, wherein said part comprises one or more cells of a plant part selected from the group consisting of a leaf, pollen, an embryo, a root, a root tip, an anther, a flower, and a fruit.

14. The fertile interspecific hybrid pepper plant, or the part thereof, of claim 13, wherein said one or more cells are a culture of regenerable cells.

15. A fertile interspecific hybrid pepper plant, or a part thereof, produced by a method of preparing a hybrid between *C. annuum* and *C. pubescens* using a bridging species, said method comprising:
(a) performing a first cross between a *C. annuum* plant or a *C. annuum* hybrid and a plant of a bridging *Capsicum* species *C. chinense* to form a *C. annuum* hybrid;
(b) crossing one or more progeny from said first cross with a *C. pubescens* plant or *C. pubescens* hybrid; and
(c) rescuing embryonic tissue from a seed produced by said crossing in step (b)to form said hybrid between *C. annuum* and *C. pubescens*;
wherein said fertile interspecific hybrid plant has no nuclear genetic material unique to *C. eximium* and does not have a *C. eximium* plant as an ancestor.

16. The fertile interspecific hybrid pepper plant, or the part thereof, of claim 15, wherein said fertile interspecific hybrid pepper plant has one or more traits selected from the group consisting of resistance to geminivirus, resistance to tobamovirus, resistance to *Xanthomonas*, resistance to aphids, resistance to powdery mildew, ease of fruit shedding, cold tolerance, purple flower, purple style, purple anther, purple filament, leaf wrinkle, black seed color, thick fruit walls, and the clustering of seed-bearing placental tissue close to the stem of the fruit.

17. The fertile interspecific hybrid pepper plant, or the part thereof, of claim 15, wherein said fertile interspecific hybrid pepper plant produces a sweet pepper fruit, a mild pepper fruit, a medium pepper fruit, a hot pepper fruit, or a very hot pepper fruit; wherein said pepper fruit has a shape selected from the group consisting of block, pointed and round; and wherein said pepper fruit has a color selected from the group consisting of green, red, yellow, orange, purple, brown and white.

18. The fertile interspecific hybrid pepper plant, or the part thereof, of claim 15. comprising nuclear DNA derived from a *C. pubescens* plant wherein the amount of said nuclear DNA is selected from the group consisting of about 0.2%, 0.5%, 1%, 2%, 5%, 7.5%, 10%, 15%, 20%, and 25%.

19. The fertile interspecific hybrid pepper plant, or the part thereof, of claim 15, wherein said part comprises one or more cells of a plant part selected from the group consisting of a leaf, pollen, an embryo, a root, a root tip, an anther, a flower, and a fruit.

20. The fertile interspecific hybrid pepper plant, or the part thereof, of claim 19, wherein said one or more cells are a culture of regenerable cells.

21. The fertile interspecific hybrid pepper plant, or the part thereof, of claim 3, wherein said fertile interspecific hybrid pepper plant has one or more traits from said *C. pubescens* parent and said trait is selected from the group consisting of leaf hair, fruit color, and flavor.

22. The fertile interspecific hybrid pepper plant, or the part thereof, of claim 10, wherein said fertile interspecific hybrid pepper plant has one or more traits from said *C. pubescens* parent and said trait is selected from the group consisting of leaf hair, fruit color, and flavor.

23. The fertile interspecific hybrid pepper plant, or the part thereof, of claim 16, wherein said fertile interspecific hybrid pepper plant has one or more traits from said *C. pubescens* parent and said trait is selected from the group consisting of leaf hair, fruit color, and flavor.

24. The fertile interspecific hybrid pepper plant, or the part thereof, of claim 2, wherein said fertile interspecific $F_1$ hybrid plant has no nuclear genetic material unique to one or more species selected from the group consisting of *Capsicum tovarii* and *Capsicum cardenasii*.

25. The fertile interspecific hybrid pepper plant, or the part thereof, of claim 9, wherein said fertile interspecific $F_1$ hybrid plant has no nuclear genetic material unique to one or more species selected from the group consisting of *C. tovarii* and *C. cardenasii*.

26. The fertile interspecific hybrid pepper plant, or the part thereof, of claim 15, wherein said fertile interspecific hybrid plant has no nuclear genetic material unique to *C. tovarii*.

27. A hybrid pepper seed wherein said hybrid pepper seed produces the fertile interspecific hybrid pepper plant of claim 2.

28. A hybrid pepper seed wherein said hybrid pepper seed produces the fertile interspecific hybrid pepper plant of claim 9.

29. A hybrid pepper seed wherein said hybrid pepper seed produces the fertile interspecific hybrid pepper plant of claim 15.

30. The method of claim 1, wherein step (b) further comprises repeating pollination of the auxin-treated flower.

31. The method of claim 8, wherein said flower bud is cultured in a medium comprising auxin and cytokinin to obtain said *C. annuum* flower.

32. A fertile interspecific hybrid pepper plant of *C. annuum* and *C. pubescens*, or a part thereof, wherein said fertile interspecific hybrid plant has no nuclear genetic material unique to *Capsicum eximium* or *C. cardenasii* and does not have a *C. eximium* or *C. cardenasii* plant as an ancestor.

33. The fertile interspecific hybrid pepper plant of claim 32, wherein said plant comprises nuclear genetic material from only one bridging species, and wherein said bridging species is *C. chinense*.

34. A method of preparing a fertile interspecific hybrid between *C. annuum* and *C. pubescens* using a bridging species comprising:
(a) performing a first cross between a *C. annuum* plant or a *C. annuum* hybrid and a plant of a bridging *Capsicum* species *C. chinense* to form a *C. annuum* hybrid;
(b) crossing one or more progeny from said first cross with a *C. pubescens* plant or *C. pubescens* hybrid; and
(c) rescuing embryonic tissue from a seed produced by said crossing in step (b) to form said hybrid between *C. annuum* and *C. pubescens*;
wherein said fertile interspecific hybrid plant has no nuclear genetic material unique to *C. eximium* and does not have a *C. eximium* plant as an ancestor.

35. A fertile interspecific hybrid pepper plant, or a part thereof, produced by a method of preparing a hybrid between *C. annuum* and *C. pubescens* using a bridging species, said method comprising:

(a) performing a first cross between a *C. pubescens* plant or a *C. pubescens* hybrid and a plant of a bridging *Capsicum* species *C. cardenasii* to form a *C. pubescens* hybrid;

(b) crossing one or more progeny from said first cross with a *C. annuum* plant or *C. annuum* hybrid; and (c) rescuing embryonic tissue from a seed produced by said crossing in step (b) to form said hybrid between *C. annuum* and *C. pubescens;* wherein said fertile interspecific hybrid plant has no nuclear genetic material unique to *C. eximium* and does not have a *C. eximium* plant as an ancestor.

36. A method of preparing a fertile interspecific hybrid between *C. annuum* and *C. pubescens* using a bridging species comprising:

(a) performing a first cross between a *C. pubescens* plant or a *C. pubescens* hybrid and a plant of a bridging *Capsicum* species *C. cardenasii* to form a *C. pubescens* hybrid;

(b) crossing one or more progeny from said first cross with a *C. annuum* plant or *C. annuum* hybrid; and (c) rescuing embryonic tissue from a seed produced by said crossing in step (b) to form said hybrid between *C. annuum* and *C. pubescens;* wherein said fertile interspecific hybrid plant has no nuclear genetic material unique to *C. eximium* and does not have a *C. eximium* plant as an ancestor.

* * * * *